United States Patent [19]
Hoffmann

[11] Patent Number: 5,831,017
[45] Date of Patent: Nov. 3, 1998

[54] OBESITY PROTEIN ANALOG COMPOUNDS AND FORMULATIONS THEREOF

[75] Inventor: James Arthur Hoffmann, Greenwood, Ind.

[73] Assignee: Eli Lilly and Company, Indianapolis, Ind.

[21] Appl. No.: 788,943

[22] Filed: Jan. 24, 1997

Related U.S. Application Data

[60] Provisional application No. 60/011,055 Jun. 25, 1996.
[51] Int. Cl.⁶ .......................... A61K 38/00; C07K 5/00; C07K 7/00; C07K 16/00
[52] U.S. Cl. .......................... 530/350; 530/324; 514/12
[58] Field of Search ................... 530/324, 350; 514/12

[56] References Cited

U.S. PATENT DOCUMENTS 5,569,603  10/1996  Tripp et al. ........................ 435/240.1

FOREIGN PATENT DOCUMENTS

| | | |
|---|---|---|
| 0 725 078 A1 | 1/1996 | European Pat. Off. . |
| 0 741 187 A2 | 11/1996 | European Pat. Off. . |
| 0 743 321 | 11/1996 | European Pat. Off. . |
| 0 744 408 | 11/1996 | European Pat. Off. . |
| 0 764 722 | 3/1997 | European Pat. Off. . |
| 2 292 382 | 8/1995 | United Kingdom . |
| WO 96/05309 | 2/1996 | WIPO . |
| WO 96/22308 | 7/1996 | WIPO . |
| WO 96/23515 | 8/1996 | WIPO . |
| WO 96/23517 | 8/1996 | WIPO . |
| WO 96/35787 | 11/1996 | WIPO . |
| WO 97/18833 | 5/1997 | WIPO . |
| WO 97/20933 | 6/1997 | WIPO . |

OTHER PUBLICATIONS

Wang, et al. Parenteral Formulations of Proteins and Peptides: Stability and Stabilizers. *Journal of Parenteral Science and Technology* 42 (2S) :S1–S26 (1988).

Wang, et al. "Review of Excipients and pH's for Parenteral Products Used in the United States" *Journal of the Parenteral Drug Association* 34(6) :452–462 (1980).

Joseph Tami and Ronald Evens. "Evaluation of Biotechnology Products" *Pharmacotherapy* 16 (4) :527–536 (1996).

Zhang, et al. "Position of the Mouse *Obese* Gene and its Human Homologue". *Nature*. 372(6505) :425–432 (1994).

Murakami and Shima. "Cloning of Rat Obese cDNA and its Expression in Obese Rats". *Biochem. Biophy. Res. Commun.* 209(3) :944–952 (26 Apr. 1995).

Pelleymounter, et al. "Effects of the Obese Gene Product on Body Weight Regulation in ob/ob Mice", *Science.* 209:540–543 (28 Jul. 1995).

Marx, "Obesity Gene Discovery May Help Solve Weighty Problem", *Science*, vol. 266:1477–1478 (2 Dec. 1994).

Rink. "In Search of a Satiety Factor", *Nature,* vol. 372(1) :406–407 (1 Dec. 1994).

Zhang et al. "Position of the Mouse *Obese* Gene and its Human Homologue", *Nature* 372 (6505) , 425–432 (1994).

Marx. Obesity Gene Discovery May Help Solve Weight Problem. *Science.* vol. 266: 1477–1478 (2 Dec. 1994).

Rink. "In Search of a Satiety Factor", *Nature* vol. 372 (1): 406–407 (1 Dec. 1994).

*Primary Examiner*—Cecilia Tsang
*Assistant Examiner*—S. G. Marshall
*Attorney, Agent, or Firm*—James J. Kelley; Steven P. Caltrider; David E. Boone

[57] ABSTRACT

The present invention provides novel compounds, which comprise an obesity protein analog complexed with a divalent metal cation, pharmaceutical formulations thereof, and methods of using such compounds for treating obesity, and disorders associated with obesity such as diabetes, cardiovascular disease and cancer.

18 Claims, No Drawings

OBESITY PROTEIN ANALOG COMPOUNDS AND FORMULATIONS THEREOF

This application claims the benefit of U.S. Provisional Application No. 60/011,055, filed Jan. 25, 1996.

FIELD OF INVENTION

The present invention is in the field of human medicine, particularly in the treatment of obesity and disorders associated with obesity. More specifically, the present invention relates to compounds and formulations of an obesity protein analog.

BACKGROUND OF THE INVENTION

Obesity, and especially upper body obesity, is a common and very serious public health problem in the United States and throughout the world. According to recent statistics, more than 25% of the United States population and 27% of the Canadian population are overweight. Kuczmarski, *Amer. J. of Clin. Nutr.* 55: 495S–502S (1992); Reeder et. al., *Can. Med. Ass. J.*, 23: 226–233 (1992). Upper body obesity is the strongest risk factor known for type II diabetes mellitus, and is a strong risk factor for cardiovascular disease and cancer as well. Recent estimates for the medical cost of obesity are $150,000,000,000 world wide. The problem has become serious enough that the surgeon general has begun an initiative to combat the ever increasing adiposity rampant in American society.

Much of this obesity induced pathology can be attributed to the strong association with dyslipidemia, hypertension, and insulin resistance. Many studies have demonstrated that reduction in obesity by diet and exercise reduces these risk factors dramatically. Unfortunately, these treatments are largely unsuccessful with a failure rate reaching 95%. This failure may be due to the fact that the condition is strongly associated with genetically inherited factors that contribute to increased appetite, preference for highly caloric foods, reduced physical activity, and increased lipogenic metabolism. This indicates that people inheriting these genetic traits are prone to becoming obese regardless of their efforts to combat the condition. Therefore, a pharmacological agent that can correct this adiposity handicap and allow the physician to successfully treat obese patients in spite of their genetic inheritance is needed.

The ob/ob mouse is a model of obesity and diabetes that is known to carry an autosomal recessive trait linked to a mutation in the sixth chromosome. Recently, Yiying Zhang and co-workers published the positional cloning of the mouse gene linked with this condition. Yiying Zhang et al. *Nature* 372: 425–32 (1994). This report disclosed the murine and human protein expressed in adipose tissue. Likewise, Murakami et al., in *Biochemical and Biophysical Research Communications* 209(3):944–52 (1995) report the cloning and expression of the rat obese gene. The protein, which is encoded by the ob gene, has demonstrated an ability to effectively regulate adiposity in mice. Pelleymounter et al., *Science* 269: 540–543 (1995).

Obesity protein analogs have been developed and have demonstrated pharmacological activity. Some of these analogs demonstrate significant improvement in physical properties and stability making them improved pharmacological agents. Analogs included in the present invention are disclosed in Basinski et al., U.S. Ser. No. 08/383,638 and DiMarchi et al., U.S. provisional application Ser. Nos. 60/000,450 and 60/002,161 (published as WO 96/23515 and 96/23517).

The present invention provides conditions under which potency of the analog is significantly enhanced. Thus, effective pharmacological treatment may be achieved at lower doses that significantly lower the risk of toxic or other undesirable side effects. In addition, because the amount of protein administered is less, the cost of the unit dosage form to the patient is reduced. Accordingly, the present invention provides a novel protein-cation complex, which comprises an obesity protein analog complexed with a divalent metal cation, pharmaceutical formulations thereof, and methods of using such compounds for the treatment of obesity, and disorders associated with obesity such as diabetes, cardiovascular disease and cancer.

SUMMARY OF THE INVENTION

The invention provides a compound comprising an obesity protein analog complexed with a divalent metal cation.

The invention additionally provides parenteral pharmaceutical formulations comprising the protein-cation compounds and methods of using such compounds for treating obesity and disorders associated with obesity such as diabetes, cardiovascular disease and cancer. The invention further provides a process of preparing such compounds, which comprises combining an obesity protein analog and a divalent metal cation in an aqueous solution at a pH of about 4.5 to 9.0.

DETAILED DESCRIPTION AND PREFERRED EMBODIMENTS

For purposes of the present invention, as disclosed and claimed herein, the following terms and abbreviations are defined as follows:

Base pair (bp)—refers to DNA or RNA. The abbreviations A,C,G, and T correspond to the 5'-monophosphate forms of the nucleotides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the nucleosides uracil, cytidine, guanine, and thymine, respectively when they occur in RNA molecules. In double stranded DNA, base pair may refer to a partnership of A with T or C with G. In a DNA/RNA heteroduplex, base pair may refer to a partnership of T with U or C with G.

Obesity protein analog—refers to a protein of the Formula (I):

(SEQ ID NO: 1)

| | | | | 5 | | | | | 10 | | | | | 15 | (I) |
|---|---|---|---|---|---|---|---|---|---|---|---|---|---|---|---|
| Val | Pro | Ile | Gln | Lys | Val | Gln | Asp | Asp | Thr | Lys | Thr | Leu | Ile | Lys | Thr |

| | | | 20 | | | | | 25 | | | | | 30 | | |
|---|---|---|---|---|---|---|---|---|---|---|---|---|---|---|---|
| Ile | Val | Thr | Arg | Ile | Asn | Asp | Ile | Ser | His | Thr | Xaa | Ser | Val | Ser | Ser |

-continued
(SEQ ID NO: 1)

|  | | 35 | | | | | 40 | | | | | 45 | | | |
|---|---|---|---|---|---|---|---|---|---|---|---|---|---|---|---|
| Lys | Gln | Lys | Val | Thr | Gly | Leu | Asp | Phe | Ile | Pro | Gly | Leu | His | Pro | Ile |
|  | 50 | | | | 55 | | | | | 60 | | | | | |
| Leu | Thr | Leu | Ser | Lys | Met | Asp | Gln | Thr | Leu | Ala | Val | Tyr | Gln | Gln | Ile |
| 65 | | | | | 70 | | | | | 75 | | | | | 80 |
| Leu | Thr | Ser | Met | Pro | Ser | Arg | Asn | Val | Ile | Gln | Ile | Ser | Asn | Asp | Leu |
|  | | | | 85 | | | | | 90 | | | | | 95 | |
| Glu | Asn | Leu | Arg | Asp | Leu | Leu | His | Val | Leu | Ala | Phe | Ser | Lys | Ser | Cys |
|  | | | 100 | | | | | 105 | | | | | 110 | | |
| His | Leu | Pro | Trp | Ala | Ser | Gly | Leu | Glu | Thr | Leu | Asp | Ser | Leu | Gly | Gly |
|  | | 115 | | | | | 120 | | | | | 125 | | | |
| Val | Leu | Glu | Ala | Ser | Gly | Tyr | Ser | Thr | Glu | Val | Val | Ala | Leu | Ser | Arg |
|  | 130 | | | | | 135 | | | | | 140 | | | | |
| Leu | Gln | Gly | Ser | Leu | Gln | Asp | Met | Leu | Trp | Gln | Leu | Asp | Leu | Ser | Pro |
| 145 | | | | | | | | | | | | | | | |
| Gly | Cys | | | | | | | | | | | | | | | wherein:
xaa at position 28 is Gln or absent;
said protein having at least one of the following substitutions:
Gln at position 4 is replaced with Glu;
Gln at position 7 is replaced with Glu;
Asn at position 22 is replaced with Gln or Asp;
Thr at position 27 is replaced with Ala;
Xaa at position 28 is replaced with Glu;
Gln at position 34 is replaced with Glu;
Met at position 54 is replaced with methionine sulfoxide, Leu, Ile, Val, Ala, or Gly;
Gln at position 56 is replaced with Glu;
Gln at position 62 is replaced with Glu;
Gln at position 63 is replaced with Glu;
Met at position 68 is replaced with methionine sulfoxide, Leu, Ile, Val, Ala, or Gly;
Asn at position 72 is replaced with Gln, Glu, or Asp;
Gln at position 75 is replaced with Glu;
Ser at position 77 is replaced with Ala;
Asn at position 78 is replaced with Gln or Asp;
Asn at position 82 is replaced with Gln or Asp;
His at position 97 is replaced with Gln, Asn, Ala, Gly, Ser, or Pro;
Trp at position 100 is replaced with Ala, Glu, Asp, Asn, Met, Ile, Phe, Tyr, Ser, Thr, Gly, Gln, Val or Leu;
Ala at position 101 is replaced with Ser, Asn, Gly, His, Pro, Thr, or Val;
Ser at position 102 is replaced with Arg;
Gly at position 103 is replaced with Ala;
Glu at position 105 is replaced with Gln;
Thr at position 106 is replaced with Lys or Ser;
Leu at position 107 is replaced with Pro;
Asp at position 108 is replaced with Glu;
Gly at position 111 is replaced with Asp;
Gly at position 118 is replaced with Leu;
Gln at position 130 is replaced with Glu;
Gln at position 134 is replaced with Glu;
Met at position 136 is replaced with methionine sulfoxide, Leu, Ile, Val, Ala, or Gly;
Trp at position 138 is replaced with Ala, Glu, Asp, Asn, Met, Ile, Phe, Tyr, Ser, Thr, Gly, Gln, Val or Leu; or
Gln at position 139 is replaced with Glu; or a pharmaceutically acceptable salt thereof.

Plasmid—an extrachromosomal self-replicating genetic element.

Reading frame—the nucleotide sequence from which translation occurs "read" in triplets by the translational apparatus of tRNA, ribosomes and associated factors, each triplet corresponding to a particular amino acid. Because each triplet is distinct and of the same length, the coding sequence must be a multiple of three. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" must be maintained. In the creation of fusion proteins containing a chelating peptide, the reading frame of the DNA sequence encoding the structural protein must be maintained in the DNA sequence encoding the chelating peptide.

Recombinant DNA Cloning Vector—any autonomously replicating agent including, but not limited to, plasmids and phages, comprising a DNA molecule to which one or more additional DNA segments can or have been added.

Recombinant DNA Expression Vector—any recombinant DNA cloning vector in which a promoter has been incorporated.

Replicon—A DNA sequence that controls and allows for autonomous replication of a plasmid or other vector.

Transcription—the process whereby information contained in a nucleotide sequence of DNA is transferred to a complementary RNA sequence.

Translation—the process whereby the genetic information of messenger RNA is used to specify and direct the synthesis of a polypeptide chain.

Vector—a replicon used for the transformation of cells in gene manipulation bearing polynucleotide sequences corresponding to appropriate protein molecules which, when combined with appropriate control sequences, confer specific properties on the host cell to be transformed. Plasmids, viruses, and bacteriophage are suitable vectors, since they are replicons in their own right. Artificial vectors are constructed by cutting and joining DNA molecules from different sources using restriction enzymes and ligases. Vectors include Recombinant DNA cloning vectors and Recombinant DNA expression vectors.

Treating—as used herein, describes the management and care of a patient for the purpose of combating the disease, condition, or disorder and includes the administration of a protein of present invention to prevent the onset of the symptoms or complications, alleviating the symptoms or complications, or eliminating the disease, condition, or disorder. Treating as used herein includes the administration of the protein for cosmetic purposes. A cosmetic purpose seeks to control the weight of a mammal to improve bodily appearance.

Isotonicity agent—isotonicity agent refers to an agent that is physiologically tolerated and embarks a suitable tonicity to the formulation to prevent the net flow of water across the cell membrane. Compounds, such as glycerin, are commonly used for such purposes at known concentrations. Other possible isotonicity agents include salts, e.g., NaCl, dextrose, and lactose.

Physiologically tolerated buffer—a physiologically tolerated buffer is known in the art. Physiologically tolerated buffers include TRIS, sodium acetate, sodium phosphate, or sodium citrate. The selection and concentration of buffer is known in the art.

Pharmaceutically acceptable preservative—a multi-use parenteral formulation must meet guidelines for preservative effectiveness to be a commercially viable product. Pharmaceutically acceptable preservatives known in the art as being acceptable in parenteral formulations include: phenol, m-cresol, benzyl alcohol, methylparaben, chlorobutanol, p-cresol, phenylmercuric nitrate, thimerosal and various mixtures thereof. Other preservatives may be found, e.g., in WALLHAUSER, K.-H., DEVELOP. BIOL. STANDARD. 24, pp. 9–28 (Basel, S. Krager, 1974). The concentration necessary to achieve preservative effectiveness is dependent upon the preservative used and the conditions of the formulation.

The nucleotide and amino acid abbreviations used herein are accepted by the United States Patent and Trademark Office as set forth in 37 C.F.R. §1.822 (b)(2) (1993). Unless otherwise indicated the amino acids are in the L configuration.

As noted above, the invention provides a compound comprising an obesity protein analog complexed with a divalent metal cation. When complexed with a divalent metal cation, the obesity protein analog demonstrates significantly enhanced potency.

Preferred proteins of the present invention are those of Formula I, wherein:
Gln at position 4 is replaced with Glu;
Gln at position 7 is replaced with Glu;
Asn at position 22 is replaced with Gln or Asp;
Thr at position 27 is replaced with Ala;
Gln at position 28 is replaced with Glu;
Gln at position 34 is replaced with Glu;
Met at position 54 is replaced with methionine sulfoxide, Leu, or Ala;
Gln at position 56 is replaced with Glu;
Gln at position 62 is replaced with Glu;
Gln at position 63 is replaced with Glu;
Met at position 68 is replaced with methionine sulfoxide, or Leu;
Asn at position 72 is replaced with Glu or Asp;
Gln at position 75 is replaced with Glu;
Asn at position 78 is replaced with Gln or Asp;
Asn at position 82 is replaced with Gln or Asp;
Gln at position 130 is replaced with Glu;
Gln at position 134 is replaced with Glu;
Met at position 136 is replaced with methionine sulfoxide, Leu, Ile; or
Gln at position 139 is replaced with Glu.

Other preferred proteins are those of Formula I wherein:
Asn at position 22 is replaced with Gln or Asp;
Thr at position 27 is replaced with Ala;
Met at position 54 is replaced with methionine sulfoxide, Leu, or Ala;
Met at position 68 is replaced with methionine sulfoxide, or Leu;
Asn at position 72 is replaced with Glu or Asp;
Asn at position 78 is replaced with Gln or Asp;
Asn at position 82 is replaced with Gln or Asp; or
Met at position 136 is replaced with methionine sulfoxide, Leu, or Ile.

Still yet additional preferred proteins are those of Formula I, wherein:
Asn at position 22 is replaced with Gln or Asp;
Thr at position 27 is replaced with Ala;
Met at position 54 is replaced with Leu, or Ala;
Met at position 68 is replaced with Leu;
Asn at position 72 is replaced with Gln or Asp;
Asn at position 78 is replaced with Gln or Asp;
Asn at position 82 is replaced with Gln or Asp; or
Met at position 136 is replaced with Leu, or Ile.

Preferred species within Formula I include species of SEQ ID NO: 2 and SEQ ID NO: 3:

(SEQ ID NO: 2)

| | | | | 5 | | | | | 10 | | | | | 15 | |
|---|---|---|---|---|---|---|---|---|---|---|---|---|---|---|---|
| Val | Pro | Ile | Gln | Lys | Val | Gln | Asp | Asp | Thr | Lys | Thr | Leu | Ile | Lys | Thr |
| | | | 20 | | | | | 25 | | | | | 30 | | |
| Ile | Val | Thr | Arg | Ile | Asp | Asp | Ile | Ser | His | Thr | Gln | Ser | Val | Ser | Ser |
| | | 35 | | | | | 40 | | | | | 45 | | | |
| Lys | Gln | Lys | Val | Thr | Gly | Leu | Asp | Phe | Ile | Pro | Gly | Leu | His | Pro | Ile |
| | 50 | | | | | 55 | | | | | 60 | | | | |
| Leu | Thr | Leu | Ser | Lys | Met | Asp | Gln | Thr | Leu | Ala | Val | Tyr | Gln | Gln | Ile |
| 65 | | | | | 70 | | | | | 75 | | | | | 80 |
| Leu | Thr | Ser | Met | Pro | Ser | Arg | Asn | Val | Ile | Gln | Ile | Ser | Asn | Asp | Leu |
| | | | | 85 | | | | | 90 | | | | | 95 | |
| Glu | Asn | Leu | Arg | Asp | Leu | Leu | His | Val | Leu | Ala | Phe | Ser | Lys | Ser | Cys |
| | | | 100 | | | | | 105 | | | | | 110 | | |
| His | Leu | Pro | Trp | Ala | Ser | Gly | Leu | Glu | Thr | Leu | Asp | Ser | Leu | Gly | Gly |

-continued

```
         115                      120                    125
Val Leu  Glu Ala Ser Gly Tyr Ser  Thr Glu Val Val Ala    Leu Ser Arg 130                      135                  140
Leu Gln  Gly Ser Leu Gln Asp  Met Leu Trp Gln Leu  Asp Leu Ser Pro

145
Gly Cys
```

(SEQ ID NO: 3)

```
                    5                        10                  15
Val Pro Ile  Gln    Lys Val Gln Asp Asp       Thr Lys Thr Leu Ile Lys Thr 20                     25                   30
Ile Val  Thr Arg Ile Asn Asp Ile Ser His Ala Gln Ser Val Ser Ser 35                     40                 45
Lys Gln  Lys Val Thr Gly Leu Asp Phe Ile Pro Gly Leu His Pro Ile 50                   55                 60
Leu Thr  Leu Ser Lys Met Asp Gln Thr Leu Ala Val Tyr Gln Gln Ile 65                  70                   75                    80
Leu Thr Ser Met    Pro Ser Arg Asn Val    Ile Gln Ile Ser Asn    Asp Leu 85                      90                  95
Glu Asn Leu     Arg Asp Leu Leu His Val  Leu Ala Phe Ser Lys Ser Cys 100                     105                  110
His Leu  Pro Trp Ala Ser Gly Leu Glu Thr Leu Asp Ser Leu Gly Gly 115                     120                  125
Val Leu  Glu Ala Ser Gly Tyr Ser Thr Glu Val Val Ala Leu Ser Arg 130                     135                  140
Leu Gln  Gly Ser Leu Gln Asp Met Leu Trp Gln Leu Asp Leu Ser Pro

145
Gly Cys
```

Most significantly, other preferred proteins of the present invention are specific substitutions to amino acid residues 97 to 111, and/or 138 of the proteins of SEQ ID NO: 1. These substitutions result in additional protein stability and are superior therapeutic agents. Accordingly, preferred embodiments are compounds comprising proteins of the Formula II:

(SEQ ID NO: 4)

```
                          5                      10                  15     (II)
        Val Pro Ile  Gln  Lys Val Gln Asp Asp    Thr Lys Thr Leu Ile Lys Thr 20                     25                   30
        Ile Val  Thr Arg Ile Asn Asp Ile Ser His Thr Xaa Ser Val Ser Ser 35                     40                 45
        Lys Gln  Lys Val Thr Gly Leu Asp Phe Ile Pro Gly Leu His Pro Ile 50                     55                 60
        Leu Thr  Leu Ser Lys Met Asp Gln Thr Leu Ala Val Tyr Gln Gln Ile 65                  70                   75                    80
        Leu Thr Ser Met    Pro Ser Arg Asn Val   Ile Gln Ile Ser Asn    Asp Leu 85                     90                    95
        Glu Asn Leu      Arg Asp Leu Leu His Val Leu Ala Phe Ser Lys   Ser Cys 100                    105                  110
        His Leu  Pro Trp Ala Ser Gly Leu Glu Thr Leu Asp Ser Leu Gly Gly 115                    120                  125
        Val Leu  Glu Ala Ser Gly Tyr Ser Thr Glu Val Val Ala Leu Ser Arg 130                    135                  140
        Leu Gln  Gly Ser Leu Gln Asp Met Leu Trp Gln Leu Asp Leu Ser Pro

145
        Gly Cys
``` wherein:

Xaa at position 28 is Gln or absent; said protein having at least one substitution selected from the group consisting of:

His at position 97 is replaced with Gln, Asn, Ala, Gly, Ser, or Pro;
Trp at position 100 is replaced with Ala, Glu, Asp, Asn, Met, Ile, Phe, Tyr, Ser, Thr, Gly, Gln, Val or Leu;
Ala at position 101 is replaced with Ser, Asn, Gly, His, Pro, Thr, or Val;
Ser at position 102 is replaced with Arg;
Gly at position 103 is replaced with Ala;
Glu at position 105 is replaced with Gln;
Thr at position 106 is replaced with Lys or Ser;
Leu at position 107 is replaced with Pro;
Asp at position 108 is replaced with Glu;
Gly at position 111 is replaced with Asp; or
Trp at position 138 is replaced with Ala, Glu, Asp, Asn, Met, Ile, Phe, Tyr, Ser, Thr, Gly, Gln, Val or Leu; or a pharmaceutically acceptable salt thereof.

Preferred proteins are a protein of the Formula III:

(SEQ ID NO: 5)

```
                  5                         10                    15        (III)
Val  Pro  Ile  Gln  Lys  Val  Gln  Asp  Asp  Thr  Lys  Thr  Leu  Ile  Lys  Thr 20                    25                    30
Ile  Val  Thr  Arg  Ile  Asp  Asp  Ile  Ser  His  Thr  Gln  Ser  Val  Ser  Ser 35                    40                    45
Lys  Gln  Lys  Val  Thr  Gly  Leu  Asp  Phe  Ile  Pro  Gly  Leu  His  Pro  Ile 50                    55                    60
Leu  Thr  Leu  Ser  Lys  Met  Asp  Gln  Thr  Leu  Ala  Val  Tyr  Gln  Gln  Ile 65                         70                    75                         80
Leu  Thr  Ser  Met  Pro  Ser  Arg  Asn  Val  Ile  Gln  Ile  Ser  Asn  Asp  Leu 85                         90                    95
Glu  Asn  Leu  Arg  Asp  Leu  Leu  His  Val  Leu  Ala  Phe  Ser  Lys  Ser  Cys 100                        105                   110
His  Leu  Pro  Trp  Ala  Ser  Gly  Leu  Glu  Thr  Leu  Asp  Ser  Leu  Gly  Gly 115                   120                   125
Val  Leu  Glu  Ala  Ser  Gly  Tyr  Ser  Thr  Glu  Val  Val  Ala  Leu  Ser  Arg 130                        135                   140
Leu  Gln  Gly  Ser  Leu  Gln  Asp  Met  Leu  Trp  Gln  Leu  Asp  Leu  Ser  Pro

145
Gly  Cys
``` said protein having at least one substitution selected from the group consisting of:

His at position 97 is replaced with Gln, Asn, Ala, Gly, Ser, or Pro;
Trp at position 100 is replaced with Ala, Glu, Asp, Asn, Met, Ile, Phe, Tyr, Ser, Thr, Gly, Gln, Val or Leu;
Ala at position 101 is replaced with Ser, Asn, Gly, His, Pro, Thr, or Val;
Ser at position 102 is replaced with Arg;
Gly at position 103 is replaced with Ala;
Glu at position 105 is replaced with Gln;
Thr at position 106 is replaced with Lys or Ser;
Leu at position 107 is replaced with Pro;
Asp at position 108 is replaced with Glu;
Gly at position 111 is replaced with Asp; or
Trp at position 138 is replaced with Ala, Glu, Asp, Asn, Met, Ile, Phe, Tyr, Ser, Thr, Gly, Gln, Val or Leu;
or a pharmaceutically acceptable salt thereof.

more preferred proteins of the Formula III are those herein:

His at position 97 is replaced with Gln, Asn, Ala, Gly, Ser or Pro;
Trp at position 100 is replaced with Ala, Glu, Asp, Asn, Met, Ile, Phe, Tyr, Ser, Thr, Gly, Gln or Leu;
Ala at position 101 is replaced with Ser, Asn, Gly, His, Pro, Thr or Val;
Glu at position 105 is replaced with Gln;
Thr at position 106 is replaced with Lys or Ser;
Leu at position 107 is replaced with Pro;
Asp at position 108 is replaced with Glu;
Gly at position 111 is replaced with Asp; or
Trp at position 138 is replaced with Ala, Glu, Asp, Asn, Met, Ile, Phe, Tyr, Ser, Thr, Gly, Gln, Val or Leu.

Other preferred proteins of the Formula III are those wherein:

His at position 97 is replaced with Ser or Pro;
Trp at position 100 is replaced with Ala, Gly, Gln, Val, Ile, or Leu;
Ala at position 101 is replaced with Thr; or
Trp at position 138 is replaced with Ala, Ile, Gly, Gln, Val or Leu.

Yet still additional preferred proteins of the Formula III are those wherein:

His at position 97 is replaced with Ser or Pro;
Trp at position 100 is replaced with Ala, Gln or Leu;
Ala at position 101 is replaced with Thr; or
Trp at position 138 is replaced with Gln.

Most preferred species of the present invention are those proteins having a di-sulfide bond between Cys at position 96 and Cys at position 146. Examples of most preferred species include species of SEQ ID NO: 6–13:

(SEQ ID NO: 6)

| | | | | 5 | | | | | 10 | | | | | 15 | |
|---|---|---|---|---|---|---|---|---|---|---|---|---|---|---|---|
| Val | Pro | Ile | Gln | Lys | Val | Gln | Asp | Asp | Thr | Lys | Thr | Leu | Ile | Lys | Thr |
| | | | 20 | | | | | 25 | | | | | 30 | | |
| Ile | Val | Thr | Arg | Ile | Asn | Asp | Ile | Ser | His | Thr | Gln | Ser | Val | Ser | Ser |
| | | 35 | | | | | 40 | | | | | 45 | | | |
| Lys | Gln | Lys | Val | Thr | Gly | Leu | Asp | Phe | Ile | Pro | Gly | Leu | His | Pro | Ile |
| | 50 | | | | | 55 | | | | | 60 | | | | |
| Leu | Thr | Leu | Ser | Lys | Met | Asp | Gln | Thr | Leu | Ala | Val | Tyr | Gln | Gln | Ile |
| 65 | | | | | 70 | | | | | 75 | | | | | 80 |
| Leu | Thr | Ser | Met | Pro | Ser | Arg | Asn | Val | Ile | Gln | Ile | Ser | Asn | Asp | Leu |
| | | | | 85 | | | | | 90 | | | | | 95 | |
| Glu | Asn | Leu | Arg | Asp | Leu | Leu | His | Val | Leu | Ala | Phe | Ser | Lys | Ser | Cys |
| | | | 100 | | | | | 105 | | | | | 110 | | |
| His | Leu | Pro | Ala | Ala | Ser | Gly | Leu | Glu | Thr | Leu | Asp | Ser | Leu | Gly | Gly |
| | | 115 | | | | | 120 | | | | | 125 | | | |
| Val | Leu | Glu | Ala | Ser | Gly | Tyr | Ser | Thr | Glu | Val | Val | Ala | Leu | Ser | Arg |
| | 130 | | | | | 135 | | | | | 140 | | | | |
| Leu | Gln | Gly | Ser | Leu | Gln | Asp | Met | Leu | Trp | Gln | Leu | Asp | Leu | Ser | Pro |
| 145 | | | | | | | | | | | | | | | |
| Gly | Cys | | | | | | | | | | | | | | | said protein having a di-sulfide bond between Cys at position 96 and Cys at position 146; or a pharmaceutically acceptable salt thereof.

(SEQ ID NO: 7)

| | | | | 5 | | | | | 10 | | | | | 15 | |
|---|---|---|---|---|---|---|---|---|---|---|---|---|---|---|---|
| Val | Pro | Ile | Gln | Lys | Val | Gln | Asp | Asp | Thr | Lys | Thr | Leu | Ile | Lys | Thr |
| | | | 20 | | | | | 25 | | | | | 30 | | |
| Ile | Val | Thr | Arg | Ile | Asp | Asp | Ile | Ser | His | Thr | Gln | Ser | Val | Ser | Ser |
| | | 35 | | | | | 40 | | | | | 45 | | | |
| Lys | Gln | Lys | Val | Thr | Gly | Leu | Asp | Phe | Ile | Pro | Gly | Leu | His | Pro | Ile |
| | 50 | | | | | 55 | | | | | 60 | | | | |
| Leu | Thr | Leu | Ser | Lys | Met | Asp | Gln | Thr | Leu | Ala | Val | Tyr | Gln | Gln | Ile |
| 65 | | | | | 70 | | | | | 75 | | | | | 80 |
| Leu | Thr | Ser | Met | Pro | Ser | Arg | Asn | Val | Ile | Gln | Ile | Ser | Asn | Asp | Leu |
| | | | | 85 | | | | | 90 | | | | | 95 | |
| Glu | Asn | Leu | Arg | Asp | Leu | Leu | His | Val | Leu | Ala | Phe | Ser | Lys | Ser | Cys |
| | | | 100 | | | | | 105 | | | | | 110 | | |
| His | Leu | Pro | Gln | Ala | Ser | Gly | Leu | Glu | Thr | Leu | Asp | Ser | Leu | Gly | Gly |
| | | 115 | | | | | 120 | | | | | 125 | | | |
| Val | Leu | Glu | Ala | Ser | Gly | Tyr | Ser | Thr | Glu | Val | Val | Ala | Leu | Ser | Arg |
| | 130 | | | | | 135 | | | | | 140 | | | | |
| Leu | Gln | Gly | Ser | Leu | Gln | Asp | Met | Leu | Trp | Gln | Leu | Asp | Leu | Ser | Pro |
| 145 | | | | | | | | | | | | | | | |
| Gly | Cys | | | | | | | | | | | | | | | said protein having a di-sulfide bond between Cys at position 96 and Cys at position 146; or a pharmaceutically acceptable salt thereof.

(SEQ ID NO: 8)

```
                  5                   10                  15
Val Pro Ile  Gln Lys Val Gln Asp Asp Thr Lys Thr Leu Ile  Lys Thr
              20                  25                  30
Ile  Val Thr Arg Ile  Asn Asp Ile  Ser His Thr Gln Ser Val Ser Ser
              35                  40                  45
Lys Gln Lys Val Thr Gly Leu Asp Phe Ile  Pro Gly Leu His Pro Ile
              50                  55                  60
Leu Thr Leu Ser Lys Met Asp Gln Thr Leu Ala Val Tyr Gln Gln Ile
              65                  70                  75              80
Leu Thr Ser Met Pro Ser Arg Asn Val Ile  Gln Ile  Ser Asn Asp Leu
                      85                  90                  95
Glu Asn Leu Arg Asp Leu Leu His Val Leu Ala Phe Ser Lys Ser Cys
                      100                 105                 110
His Leu Pro Trp Ala Ser Gly Leu Glu Thr Leu Asp Ser Leu Gly Gly
                      115                 120                 125
Val Leu Glu Ala Ser Gly Tyr Ser Thr Glu Val Val Ala Leu Ser Arg
                      130                 135                 140
Leu Gln Gly Ser Leu Gln Asp Met Leu Gln Gln Leu Asp Leu Ser Pro
145
Gly Cys
``` said protein having a di-sulfide bond between Cys at position 96 and Cys at position 146; or a pharmaceutically acceptable salt thereof.

(SEQ ID NO: 9)

```
                  5                   10                  15
Val Pro Ile  Gln Lys Val Gln Asp Asp Thr Lys Thr Leu Ile  Lys Thr
              20                  25                  30
Ile  Val Thr Arg Ile  Asn Asp Ile  Ser His Thr Gln Ser Val Ser Ser
              35                  40                  45
Lys Gln Lys Val Thr Gly Leu Asp Phe Ile  Pro Gly Leu His Pro Ile
              50                  55                  60
Leu Thr Leu Ser Lys Met Asp Gln Thr Leu Ala Val Tyr Gln Gln Ile
              65                  70                  75              80
Leu Thr Ser Met Pro Ser Arg Asn Val Ile  Gln Ile  Ser Asn Asp Leu
                      85                  90                  95
Glu Asn Leu Arg Asp Leu Leu His Val Leu Ala Phe Ser Lys Ser Cys
                      100                 105                 110
His Leu Pro Gln Ala Ser Gly Leu Glu Thr Leu Asp Ser Leu Gly Gly
                      115                 120                 125
Val Leu Glu Ala Ser Gly Tyr Ser Thr Glu Val Val Ala Leu Ser Arg
                      130                 135                 140
Leu Gln Gly Ser Leu Gln Asp Met Leu Gln Gln Leu Asp Leu Ser Pro
145
Gly Cys
``` said protein having a di-sulfide bond between Cys at position 96 and Cys at position 146; or a pharmaceutically acceptable salt thereof.

(SEQ ID NO: 10)

```
                  5                   10                  15
Val Pro Ile  Gln Lys Val Gln Asp Asp Thr Lys Thr Leu Ile  Lys Thr
              20                  25                  30
Ile  Val Thr Arg Ile  Asn Asp Ile  Ser His Ala Gln Ser Val Ser Ser
              35                  40                  45
Lys Gln Lys Val Thr Gly Leu Asp Phe Ile  Pro Gly Leu His Pro Ile
              50                  55                  60
Leu Thr Leu Ser Lys Met Asp Gln Thr Leu Ala Val Tyr Gln Gln Ile
              65                  70                  75              80
Leu Thr Ser Met Pro Ser Arg Asn Val Ile  Gln Ile  Ser Asn Asp Leu
                      85                  90                  95
Glu Asn Leu Arg Asp Leu Leu His Val Leu Ala Phe Ser Lys Ser Cys
                      100                 105                 110
His Leu Pro Ala Ala Ser Gly Leu Glu Thr Leu Asp Ser Leu Gly Gly
                      115                 120                 125
Val Leu Glu Ala Ser Gly Tyr Ser Thr Glu Val Val Ala Leu Ser Arg
                      130                 135                 140
Leu Gln Gly Ser Leu Gln Asp Met Leu Trp Gln Leu Asp Leu Ser Pro
145
Gly Cys
``` said protein having a di-sulfide bond between Cys at position 96 and Cys at position 146; or a pharmaceutically acceptable salt thereof.

(SEQ ID NO: 11)

```
                  5                   10                  15
Val Pro Ile  Gln Lys Val Gln Asp Asp Thr Lys Thr Leu Ile  Lys Thr
              20                  25                  30
Ile  Val Thr Arg Ile  Asn Asp Ile  Ser His Thr Gln Ser Val Ser Ser
              35                  40                  45
Lys Gln Lys Val Thr Gly Leu Asp Phe Ile  Pro Gly Leu His Pro Ile
              50                  55                  60
Leu Thr Leu Ser Lys Met Asp Gln Thr Leu Ala Val Tyr Gln Gln Ile
              65                  70                  75              80
Leu Thr Ser Met Pro Ser Arg Asn Val Ile  Gln Ile  Ser Asn Asp Leu
                      85                  90                  95
Glu Asn Leu Arg Asp Leu Leu His Val Leu Ala Phe Ser Lys Ser Cys
                      100                 105                 110
His Leu Pro Ala Ala Ser Gly Leu Glu Thr Leu Asp Ser Leu Gly Gly
                      115                 120                 125
Val Leu Glu Ala Ser Gly Tyr Ser Thr Glu Val Val Ala Leu Ser Arg
                      130                 135                 140
Leu Gln Gly Ser Leu Gln Asp Met Leu Gln Gln Leu Asp Leu Ser Pro
145
Gly Cys
``` said protein having a di-sulfide bond between Cys at position 96 and Cys at position 146; or a pharmaceutically acceptable salt thereof.

(SEQ ID NO: 12)

```
                  5                   10                  15
Val Pro Ile  Gln Lys Val Gln Asp Asp Thr Lys Thr Leu Ile  Lys Thr
              20                  25                  30
Ile  Val Thr Arg Ile  Asn Asp Ile  Ser His Thr Gln Ser Val Ser Ser
              35                  40                  45
Lys Gln Lys Val Thr Gly Leu Asp Phe Ile  Pro Gly Leu His Pro Ile
              50                  55                  60
Leu Thr Leu Ser Lys Met Asp Gln Thr Leu Ala Val Tyr Gln Gln Ile
```

-continued (SEQ ID NO: 12)

```
                65                  70                  75                  80
Leu Thr Ser Met Pro Ser Arg Asn Val Ile Gln Ile Ser Asn Asp Leu 85                  90                  95
Glu Asn Leu Arg Asp Leu Leu His Val Leu Ala Phe Ser Lys Ser Cys 100                 105                 110
Ser Leu Pro Gln Thr Ser Gly Leu Glu Thr Leu Asp Ser Leu Gly Gly 115                 120                 125
Val Leu Glu Ala Ser Gly Tyr Ser Thr Glu Val Val Ala Leu Ser Arg 130                 135                 140
Leu Gln Gly Ser Leu Gln Asp Met Leu Gln Gln Leu Asp Leu Ser Pro

145
Gly Cys
``` said protein having a di-sulfide bond between Cys at position 96 and Cys at position 146; or a pharmaceutically acceptable salt thereof.

(SEQ ID NO: 13)

```
            5                   10                  15
Val Pro Ile Gln Lys Val Gln Asp Asp Thr Lys Thr Leu Ile Lys Thr 20                  25                  30
Ile Val Thr Arg Ile Asn Asp Ile Ser His Thr Gln Ser Val Ser Ser 35                  40                  45
Lys Gln Lys Val Thr Gly Leu Asp Phe Ile Pro Gly Leu His Pro Ile 50                  55                  60
Leu Thr Leu Ser Lys Met Asp Gln Thr Leu Ala Val Tyr Gln Gln Ile 65                  70                  75                  80
Leu Thr Ser Met Pro Ser Arg Asn Val Ile Gln Ile Ser Asn Asp Leu 85                  90                  95
Glu Asn Leu Arg Asp Leu Leu His Val Leu Ala Phe Ser Lys Ser Cys 100                 105                 110
Ser Leu Pro Gln Ala Ser Gly Leu Glu Thr Leu Asp Ser Leu Gly Gly 115                 120                 125
Val Leu Glu Ala Ser Gly Tyr Ser Thr Glu Val Val Ala Leu Ser Arg 130                 135                 140
Leu Gln Gly Ser Leu Gln Asp Met Leu Gln Gln Leu Asp Leu Ser Pro

145
Gly Cys
``` said protein having a di-sulfide bond between Cys at position 96 and Cys at position 146; or a pharmaceutically acceptable salt thereof.

The presently claimed compounds comprise an obesity protein analog complexed with a divalent metal cation. A divalent metal cation includes, for example, $Zn^{++}$, $Mn^{++}$, $Fe^{++}$, $Co^{++}$, $Cd^{++}$, $Ni^{++}$ and the like. A combination of two or more divalent metal cations is operable; however the preferred compounds comprise a single species of metal cation, most preferably $Zn^{++}$. Preferably, the divalent metal cation is in excess; however, the molar ratio of at least one molecule of a divalent metal cation for each ten molecules of obesity protein analog is operable. Preferably, the compounds comprise from 1 to 100 divalent metal cations per molecule of obesity protein analog. The compounds may be amorphous or crystalline solids.

Appropriate forms of metals cations are any form of a divalent metal cation that is available to form a complex with a molecule of obesity protein analog of the present invention. The metal cation may be added in solid form or it may be added as a solution. Several different cationic salts can be used in the present invention. Representative examples of metal salts include the acetate, bromide, chloride, fluoride, iodide and sulfate salt forms. The skilled artisan will recognize that there are many other metal salts which also might be used in the production of the compounds of the present invention. Preferably, zinc acetate or zinc chloride is used to create the zinc-obesity protein analog compounds of the present invention. Most preferably, the divalent metal cationic salt is zinc chloride, Generally, the claimed compounds are prepared by techniques known in the art. For example, convenient preparation is to combine the obesity protein analog with the desired divalent metal cation in an aqueous solution at a pH of about 4.5–9.0, preferably about pH 5.5–8, most preferably, pH 6.5–7.6. The claimed compound precipitates from the solution as a crystalline or amorphous solid. Significantly, the compound is easily isolated and purified by conventional separation techniques appreciated in the art including filtration and centrifugation. Significantly, the protein-metal cation complex is stable and may be conveniently stored as a solid or as an aqueous suspension.

The present invention further provides a pharmaceutical formulation comprising a compound of the present invention and water. The concentration of the obesity protein analog in the formulation is about 0.1 mg/mL to about 100 mg/mL; preferably about 0.5 mg/mL to about 50.0 mg/mL; most preferably, about 5.0 mg/mL.

The formulation preferably comprises a pharmaceutically acceptable preservative at a concentration necessary to maintain preservative effectiveness. The relative amounts of preservative necessary to maintain preservative effectiveness varies with the preservative used. Generally, the amount necessary can be found in WALLHAUSER, K.-H., DEVELOP. BIOL. STANDARD. 24, pp. 9–28 (Basel, S. Krager, 1974), herein incorporated by reference.

An isotonicity agent, preferably glycerin, may be additionally added to the formulation. The concentration of the isotonicity agent is in the range known in the art for parenteral formulations, preferably about 16 mg/mL glycerin. The pH of the formulation may also be buffered with a physiologically tolerated buffer. Acceptable physiologically tolerated buffers include TRIS, sodium acetate, sodium phosphate, or sodium citrate. The selection and concentration of buffer is known in the art.

Other additives, such as a pharmaceutically acceptable excipients like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), BRIJ 35 (polyoxyethylene (23) lauryl ether), and PEG (polyethylene glycol) may optionally be added to the formulation to reduce aggregation.

The claimed pharmaceutical formulations are prepared in a manner known in the art, and are administered individually or in combination with other therapeutic agents. The formulations of the present invention can be prepared using conventional dissolution and mixing procedures. Preferably, the claimed formulations are prepared in an aqueous solution suitable for parenteral use. That is, a protein solution is prepared by mixing water for injection, buffer, and a preservative. Divalent metal cations are added to a total cation concentration of about 0.001 to 5.0 mg/mL, preferably 0.05 to 1.5 mg/mL. The pH of the solution may be adjusted to completely precipitate the obesity protein analog-zinc complex. The compound is easily resuspended before administration to the patient.

Parenteral daily doses of the compound are in the range from about 1 ng to about 10 mg per kg of body weight, although lower or higher dosages may be administered. The required dosage will be determined by the physician and will depend on the severity of the condition of the patient and upon such criteria as the patient's height, weight, sex, age, and medical history.

Variations of this process would be recognized by one of ordinary skill in the art. For example, the order the components are added, if a the surfactant is used, the temperature, and pH at which the formulation is prepared may be optimized for the concentration and means of administration used.

The pH of the formulation is generally pH 4.5 to 9.0 and preferably 5.5 to 8.0, most preferably 6.5 to 7.6; although more acidic pH wherein a portion or all of the protein-metal cation complex is in solution is operable.

The formulations prepared in accordance with the present invention may be used in a syringe, injector, pumps or any other device recognized in the art for parenteral administration.

The proteins used in the present compounds can be prepared by any of a variety of recognized peptide synthesis techniques including classical (solution) methods, solid phase methods, semi synthetic methods, and more recent recombinant DNA methods. Recombinant methods are preferred if a high yield is desired. The basic steps in the recombinant production of protein include:

a) construction of a synthetic or semi-synthetic (or isolation from natural sources) DNA encoding the obesity protein, b) integrating the coding sequence into an expression vector in a manner suitable for the expression of the protein either alone or as a fusion protein, c) transforming an appropriate eukaryotic or prokaryotic host cell with the expression vector, and d) recovering and purifying the recombinantly produced protein.

Synthetic genes, the in vitro or in vivo transcription and translation of which will result in the production of the protein may be constructed by techniques well known in the art. Owing to the natural degeneracy of the genetic code, the skilled artisan will recognize that a sizable yet definite number of DNA sequences may be constructed which encode the desired proteins. In the preferred practice of the invention, synthesis is achieved by recombinant DNA technology.

Methodology of synthetic gene construction is well known in the art. For example, see Brown, et al. (1979) Methods in Enzymology, Academic Press, N.Y., Vol. 68, pgs. 109–151. The DNA sequence corresponding to the synthetic claimed protein gene may be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404). It may be desirable in some applications to modify the coding sequence of the obesity protein so as to incorporate a convenient protease sensitive cleavage site, e.g., between the signal peptide and the structural protein facilitating the controlled excision of the signal peptide from the fusion protein construct.

The gene encoding the obesity protein may also be created by using polymerase chain reaction (PCR). The template can be a cDNA library (commercially available from CLONETECH or STRATAGENE) or mRNA isolated from the desired arrival adipose tissue. Such methodologies are well known in the art Maniatis, et al. *Molecular Cloning: A Laboratory Manual*, Cold Spring Harbor Press, Cold Spring Harbor Laboratory, Cold Spring Harbor, N.Y. (1989).

The constructed or isolated DNA sequences are useful for expressing the obesity protein either by direct expression or as fusion protein. When the sequences are used in a fusion gene, the resulting product will require enzymatic or chemical cleavage. A variety of peptidases which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See U.S. Pat. No. 5,126,249; Carter P., Site Specific Proteolysis of Fusion Proteins, Ch. 13 in *Protein Purification: From Molecular Mechanisms to Large Scale Processes*, American Chemical Soc., Washington, D.C. (1990).

Construction of suitable vectors containing the desired coding and control sequences employ standard ligation techniques. Isolated plasmids or DNA fragments are cleaved, tailored, and religated in the form desired to form the plasmids required.

To effect the translation of the desired protein, one inserts the engineered synthetic DNA sequence in any of a plethora of appropriate recombinant DNA expression vectors through the use of appropriate restriction endonucleases. A synthetic coding sequence may be designed to possess restriction endonuclease cleavage sites at either end of the transcript to facilitate isolation from and integration into these expression and amplification and expression plasmids. The isolated cDNA coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The restriction sites are chosen so as to properly orient the coding sequence with control sequences to achieve proper in-frame reading and expression of the protein.

In general, plasmid vectors containing promoters and control sequences which are derived from species compatible with the host cell are used with these hosts. The vector ordinarily carries a replication origin as well as marker sequences which are capable of providing phenotypic selection in transformed cells. For example, *E. coli* is typically transformed using pBR322, a plasmid derived from an *E. coli* species (Bolivar, et al., *Gene*2: 95 (1977)). Plasmid pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA technology.

The desired coding sequence is inserted into an expression vector in the proper orientation to be transcribed from a promoter and ribosome binding site, both of which should be functional in the host cell in which the protein is to be expressed. An example of such an expression vector is a plasmid described in Belagaje et al., U.S. Pat. No. 5,304,493, the teachings of which are herein incorporated by reference. The gene encoding A-C-B proinsulin described in U.S. Pat. No. 5,304,493 can be removed from the plasmid pRB182 with restriction enzymes NdeI and BamHI. The isolated DNA sequences can be inserted into the plasmid backbone on a NdeI/BamHI restriction fragment cassette.

In general, procaryotes are used for cloning of DNA sequences in constructing the vectors useful in the invention.

For example, *E. coli* K12 strain 294 (ATCC No. 31446) is particularly useful. Other microbial strains which may be used include *E. coli* B and *E. coli* X1776 (ATCC No. 31537). These examples are illustrative rather than limiting.

Procaryotes also are used for expression. The aforementioned strains, as well as *E. coli* W3110 (prototrophic, ATCC No. 27325), bacilli such as *Bacillus subtilis*, and other enterobacteriaceae such as *Salmonella typhimurium* or *Serratia marcescans*, and various pseudomonas species may be used. Promoters suitable for use with prokaryotic hosts include the β-lactamase (vector pGX2907 [ATCC 39344] contains the replicon and β-lactamase gene) and lactose promoter systems (Chang et al., *Nature*, 275: 615 (1978); and Goeddel et al., *Nature*281: 544 (1979)), alkaline phosphatase, the tryptophan (trp) promoter system (vector pATH1 [ATCC 37695] is designed to facilitate expression of an open reading frame as a trpE fusion protein under control of the trp promoter) and hybrid promoters such as the tac promoter (isolatable from plasmid pDR540 ATCC-37282). However, other functional bacterial promoters, whose nucleotide sequences are generally known, enable one of skill in the art to ligate them to DNA encoding the protein using linkers or adaptors to supply any required restriction sites. Promoters for use in bacterial systems also will contain a Shine-Dalgarno sequence operably linked to the DNA encoding protein.

The DNA molecules may also be recombinantly produced in eukaryotic expression systems. Preferred promoters controlling transcription in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. β-actin promoter. The early and late promoters of the SV40 virus are conveniently obtained as an SV40 restriction fragment which also contains the SV40 viral origin of replication. Fiers, et al., *Nature*, 273: 113 (1978). The entire SV40 genome may be obtained from plasmid pBRSV, ATCC 45019. The immediate early promoter of the human cytomegalovirus may be obtained from plasmid pCMBb (ATCC 77177). Of course, promoters from the host cell or related species also are useful herein.

Transcription of the DNA by higher eucaryotes is increased by inserting an enhancer sequence into the vector. Enhancers are cis-acting elements of DNA, usually about 10–300 bp, that act on a promoter to increase its transcription. Enhancers are relatively oriented and positioned independently and have been found 5' (Laimins, L. et al., *PNAS*78: 993 (1981)) and 3' (Lusky, M. L., et al., Mol. Cell Bio. 3: 1108 (1983)) to the transcription unit, within an intron (Banerji, J. L. et al., *Cell*33: 729 (1983)) as well as within the coding sequence itself (Osborne, T. F., et al., *Mol. Cell Bio.*4: 1293 (1984)). Many enhancer sequences are now known from mammalian genes (globin, RSV, SV40, EMC, elastase, albumin, alpha-fetoprotein and insulin). Typically, however, one will use an enhancer from a eukaryotic cell virus. Examples include the SV40 late enhancer, the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding protein. The 3' untranslated regions also include transcription termination sites.

Expression vectors may contain a selection gene, also termed a selectable marker. Examples of suitable selectable markers for mammalian cells are dihydrofolate reductase (DHFR, which may be derived from the BglII/HindIII restriction fragment of pJOD-10 [ATCC 68815]), thymidine kinase (herpes simplex virus thymidine kinase is contained on the BamHI fragment of vP-5 clone [ATCC 2028]) or neomycin (G418) resistance genes (obtainable from pNN414 yeast artificial chromosome vector [ATCC 37682]). When such selectable markers are successfully transferred into a mammalian host cell, the transfected mammalian host cell can survive if placed under selective pressure. There are two widely used distinct categories of selective regimes. The first category is based on a cell's metabolism and the use of a mutant cell line which lacks the ability to grow without a supplemented media. Two examples are: CHO DHFR– cells (ATCC CRL-9096) and mouse LTK– cells (L-M(TK-) ATCC CCL-2.3). These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in nonsupplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., *J. Molec. Appl. Genet.*1: 327 (1982), mycophenolic acid, Mulligan, R. C. and Berg, P. *Science*209: 1422 (1980), or hygromycin, Sugden, B. et al.,*Mol Cell. Biol.*5: 410–413 (1985). The three examples given above employ bacterial genes under eukaryotic control to convey resistance to the appropriate drug G418 or neomycin (geneticin), xgpt (mycophenolic acid) or hygromycin, respectively.

A preferred vector for eucaryotic expression is pRc/CMV. pRc/CMV is commercially available from Invitrogen Corporation, 3985 Sorrento Valley Blvd., San Diego, Calif. 92121. To confirm correct sequences in plasmids constructed, the ligation mixtures are used to transform *E. coli* K12 strain DH10B (ATCC 31446) and successful transformants selected by antibiotic resistance where appropriate. Plasmids from the transformants are prepared, analyzed by restriction and/or sequence by the method of Messing, et al., *Nucleic Acids Res.*9: 309 (1981).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan. The techniques of transforming cells with the aforementioned vectors are well known in the art and may be found in such general references as Maniatis, et al., *Molecular Cloning: A Laboratory Manual*, Cold Spring Harbor Press, Cold Spring Harbor Laboratory, Cold Spring Harbor, N.Y. (1989), or *Current Protocols in Molecular Biology* (1989) and supplements.

Preferred suitable host cells for expressing the vectors encoding the claimed proteins in higher eucaryotes include:

African green monkey kidney line cell line transformed by SV40 (COS-7, ATCC CRL-1651); transformed human primary embryonal kidney cell line 293,(Graham, F. L. et al., *J. Gen Virol.*36: 59–72 (1977), *Virology*77: 319–329, *Virology*86: 10–21); baby hamster kidney cells (BHK-21(C-13), ATCC CCL-10, *Virology* 16: 147 (1962)); Chinese hamster ovary cells CHO-DHFR− (ATCC CRL-9096), mouse Sertoli cells (TM4, ATCC CRL-1715, *Biol. Reprod.* 23: 243–250 (1980)); African green monkey kidney cells (VERO 76, ATCC CRL-1587); human cervical epitheloid carcinoma cells (HeLa, ATCC CCL-2); canine kidney cells (MDCK, ATCC CCL-34); buffalo rat liver cells (BRL 3A, ATCC CRL-1442); human diploid lung cells (WI-38, ATCC CCL-75); human hepatocellular carcinoma cells (Hep G2, ATCC HB-8065);and mouse mammary tumor cells (MMT 060562, ATCC CCL51).

In addition to prokaryotes, unicellular eukaryotes such as yeast cultures may also be used. *Saccharomyces cerevisiae*, or common baker's yeast is the most commonly used eukaryotic microorganism, although a number of other strains are commonly available. For expression in Saccharomyces, the plasmid YRp7, for example, (ATCC-40053, Stinchcomb, et al., *Nature*282: 39 (1979); Kingsman et al., *Gene*7: 141 (1979); Tschemper et al., *Gene*10: 157 (1980)) is commonly used. This plasmid already contains the trp gene which provides a selection marker for a mutant strain of yeast lacking the ability to grow in tryptophan, for example ATCC no. 44076 or PEP4-1 (Jones, *Genetics*85: 12 (1977)).

Suitable promoting sequences for use with yeast hosts include the promoters for 3-phosphoglycerate kinase (found on plasmid pAP12BD ATCC 53231 and described in U.S. Pat. No. 4,935,350, Jun. 19, 1990) or other glycolytic enzymes such as enolase (found on plasmid pAC1 ATCC 39532), glyceraldehyde-3-phosphate dehydrogenase (derived from plasmid pHcGAPC1 ATCC 57090, 57091), zymomonas mobilis (U.S. Pat. No. 5,000,000 issued Mar. 19, 1991), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which contain inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein (contained on plasmid vector pCL28XhoLHBPV ATCC 39475, U.S. Pat. No. 4,840,896), glyceraldehyde 3-phosphate dehydrogenase, and enzymes responsible for maltose and galactose (GAL1 found on plasmid pRY121 ATCC 37658) utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjunction with the CYC1 promoter on plasmid YEpsec—hI1beta ATCC 67024), also are advantageously used with yeast promoters.

Preparation 1

The plasmid containing the DNA sequence encoding the desired protein, is digested with PmlI and Bsu36I. The recognition sequences for these enzymes lie within the coding region for the protein at nucleotide positions 275 and 360 respectively. The cloning vector does not contain these recognition sequences. Consequently, only two fragments are seen following restriction enzyme digestion with PmlI and Bsu36I, one corresponding to the vector fragment, the other corresponding to the ~85 base pair fragment liberated from within the protein coding sequence. This sequence can be replaced by any DNA sequence encoding the amino acid substitutions between positions 91 and 116 of the present invention. These DNA sequences are synthesized chemically as two oligonucleotides with complementary bases and ends that are compatible with the ends generated by digestion with PmlI and Bsu36I. The chemically synthesized oligonucleotides are mixed in equimolar amounts (1–10 picomoles/microliter), heated to 95 degrees and allow to anneal by slowly decreasing the temperature to 20–25 degrees. The annealed oligonucleotides are in a standard ligation reaction. Ligation products are transformed and analyzed as described in Example 1. Other substitutions are preferably carried out in a similar manner using appropriate restriction cites.

Preparation 2

A DNA sequence encoding SEQ ID NO: 6 with a Met Arg leader sequence was obtained using the plasmid and procedures described in preparation 1. The plasmid was digested with PmlI and Bsu36I. A synthetic DNA fragment of the sequence 5"-SEQ ID NO:14:

GTGCTGGCCTTCTCTAAAAGTTGCCACTTGCCAGCTGCCAGTGGCCTGGAGACATTGGACAGTC (SEQ ID NO: 14)
TGGGGGGAGTCCTGGAAGCC annealed with the sequence 5'-SEQ ID NO:15:

TGAGGCTTCCAGGACTCCCCCCAGACTGTCCAATGTCTCCAGGCCACTGGCAGCTGGCAAGTGG (SEQ ID NO: 15)
CAACTTTTAGAGAAGGCCAGCAC was inserted between the PmlI and the Bsu36I sites. Following ligation, transformation and plasmid isolation, the sequence of the synthetic fragment was verified by DNA sequence analysis.

The techniques of transforming cells with the aforementioned vectors are well known in the art and may be found in such general references as Maniatis, et al. (1988) *Molecular Cloning: A Laboratory Manual*, Cold Spring Harbor Press, Cold Spring Harbor Laboratory, Cold Spring Harbor, N.Y. or *Current Protocols in Molecular Biology* (1989) and supplements. The techniques involved in the transformation of *E. coli* cells used in the preferred practice of the invention as exemplified herein are well known in the art. The precise conditions under which the transformed *E. coli* cells are cultured is dependent on the nature of the *E. coli* host cell line and the expression or cloning vectors employed. For example, vectors which incorporate thermoinducible promoter-operator regions, such as the c1857 thermoinducible lambda-phage promoter-operator region, require a temperature shift from about 30 to about 40 degrees C. in the culture conditions so as to induce protein synthesis.

In the preferred embodiment of the invention E. coli K12 RV308 cells are employed as host cells but numerous other cell lines are available such as, but not limited to, E. coli K12 L201, L687, L693, L507, L640, L641, L695, L814 (E. coli B). The transformed host cells are then plated on appropriate media under the selective pressure of the antibiotic corresponding to the resistance gene present on the expression plasmid. The cultures are then incubated for a time and temperature appropriate to the host cell line employed.

Proteins that are expressed in high-level bacterial expression systems characteristically aggregate in granules or inclusion bodies which contain high levels of the overexpressed protein. Kreuger et al., in *Protein Folding*, Gierasch and King, eds., pgs 136–142 (1990), American Association for the Advancement of Science Publication No. 89–18S, Washington, D.C. Such protein aggregates must be dissolved to provide further purification and isolation of the desired protein product. Id. A variety of techniques using strongly denaturing solutions such as guanidinium-HCl and/or weakly denaturing solutions such as urea are used to solubilize the proteins. Gradual removal of the denaturing agents (often by dialysis) in a solution allows the denatured protein to assume its native conformation. The particular conditions for denaturation and folding are determined by the particular protein expression system and/or the protein in question.

Preparation 3

The protein of SEQ ID NO: 6 with a Met Arg leader sequence was expressed in *E.coli* granules were isolated in 8M urea and 5 mM cysteine. The protein was purified by anion exchange chromatography in 8M urea, and folded by dilution into 8M urea (containing 5 mM cysteine) and exhaustive dialysis against PBS. Following final purification of the proteins by size exclusion chromatography the proteins were concentrated to 3–3.5 mg/mL in PBS.

Preparation 4

A DNA sequence encoding the protein of SEQ ID NO: 2 was assembled from chemically synthesized single stranded oligonucleotides to generate a double stranded DNA sequence.

The oligonucleotides used to assemble this DNA sequence are as follows:

| | |
|---|---|
| TATGAGGGTACCTATCCAAAAAGTACAAGATGACACCAAAACACTGATAAAGACAATAGTCACAAG | (SEQ ID NO: 16) |
| GATAGATGATATCTCACACACACAGTCAGTCTCATCTAAACAGAAAGTCACAGGCTTGGACTTCATACCTGG | (SEQ ID NO: 17) |
| GCTGCACCCCATACTGACATTGTCTAAAATGGACCAGACACTGGCAGTCTATCAACAGATCTTAACAAGTATGCCTT | (SEQ ID NO: 18) |
| CTAGAAGGCATACTTGTTAAGATCTGTTGATAGACTGC | (SEQ ID NO: 19) |
| CAGTGTCTGGTCCATTTTAGACAATGTCAGTATGGGGTGCAGCCCAGGTATGAAGTCCAAGC | (SEQ ID NO: 20) |
| CTGTGACTTTCTGTTTAGATGAGACTGACTGTGTGTGTGAGATATCATCTATCCTTGTGACTATTGTCTTTATCAGTGTTTG | (SEQ ID NO: 21) |
| GTGTCATCTTGTACTTTTTGGATAGGTACCCTCA | (SEQ ID NO: 22) |
| CTAGAAACGTGATACAAATATCTAACGACCTGGAGAACCTGCGGGATCTGCTGCACGTGCTGGCCTTCTCTAAAAGTTGCCACTTGCCATGG | (SEQ ID NO: 23) |
| GCCAGTGGCCTGGAGACATTGGACAGTCTGGGGGGAGTCCTGGAAGCCTCAGGCTATTCTACAGAGGTGGTGGC | (SEQ ID NO: 24) |
| CCTGAGCAGGCTGCAGGGGTCTCTGCAAGACATGCTGTGGCAGCTGGACCTGAGCCCCGGGTGCTAATAG | (SEQ ID NO: 25) |
| GATCCTATTAGCACCCGGGGCTCAGGTCCAGCTGCCACAGCATGTCTTGCAGAGACC | (SEQ ID NO: 26) |
| CCTGCAGCCTGCTCAGGGCCACCACCTCTGTAGAATAGCCTGAGGCTTCCAGGACTCCC | (SEQ ID NO: 27) |
| CCCAGACTGTCCAATGTCTCCAGGCCACTGGCCCATGGCAAGTGGCAACTTTTAGAGAAGG | (SEQ ID NO: 28) |
| CCAGCACGTGCAGCAGATCCCGCAGGTTCTCCAGGTCGTTAGATATTTGTATCACGTTT | (SEQ ID NO: 29) |

Oligonucleotides 16–22 were used to generate an approximately 220 base-pair segment which extends from the NdeI site to the XbaI site at position 220 within the coding sequence. The oligonucleotides 23–29 were used to generate an approximately 240 base-pair segment which extends from the XbaI site to the BamHI site.

To assemble the 220 and 240 base-pair fragments, the respective oligonucleotides were mixed in equimolar amounts, usually at concentrations of about 1–2 picomoles per microliters. Prior to assembly, all but the oligonucleotides at the 5"-ends of the segment were phosphorylated in standard kinase buffer with T4 DNA kinase using the conditions specified by the supplier of the reagents. The mixtures were heated to 95° C. and allowed to cool slowly to room temperature over a period of 1–2 hours to ensure proper annealing of the oligonucleotides. The oligonucleotides were then ligated to each other and into a cloning vector, PUC19 was used, but others are operable using T4 DNA ligase. The PUC19 buffers and conditions are those recommended by the supplier of the enzyme. The vector for the 220 base-pair fragment was digested with NdeI and XbaI, whereas the vector for the 240 base-pair fragment was digested with XbaI and BamHI prior to use. The ligation mixes were used to transform E. coli DH10B cells (commercially available from Gibco/BRL) and the transformed cells were plated on tryptone-yeast (TY) plates containing 100 μg/mL of ampicillin, X-gal and IPTG. Colonies which grow up overnight were grown in liquid TY medium with 100 μg/mL of ampicillin and were used for plasmid isolation and DNA sequence analysis. Plasmids with the correct sequence were kept for the assembly of the complete gene. This was accomplished by gel-purification of the 220 base-pair and the 240 base-pair fragments and ligation of these two fragments into PUC19 linearized with NdeI and BamHI. The ligation mix was transformed into E. coli DH10B cells and plated as described previously. Plasmid DNA was isolated from the resulting transformants and digested with NdeI and BglII. The large vector fragment was gel-purified and ligated with a approximately 195 base-pair segment which was assembled as described previously from six chemically synthesized oligonucleotides as show below.

| | |
|---|---|
| TAT GCG GGT ACC GAT CCA GAA AGT TCA GGA CGA CAC CAA AAC CCT GAT CAA AAC CAT CGT TAC | (SEQ ID NO: 30) |
| GCG TAT CAA CGA CAT CTC CCA CAC CCA GTC CGT GAG CTC CAA ACA GAA GGT TAC CGG TCT GGA CTT CAT CCC GG | (SEQ ID NO: 31) |
| GTC TGC ACC CGA TCC TGA CCC TGT CCA AAA TGG ACC AGA CCC TGG CTG TTT ACC AGC A | (SEQ ID NO: 32) |
| ATA CGC GTA ACG ATG GTT TTG ATC AGG GTT TTG GTG TCG TCC TGA ACT TTC TGG ATC GGT ACC CGC A | (SEQ ID NO: 33) |
| TGC AGA CCC GGG ATG AAG TCC AGA CCG GTA ACC TTC TGT TTG GAG CTC ACG GAC TGG GTG TGG GAG ATG TCG TTG | (SEQ ID NO: 34) |
| GAT CTG CTG GTA AAC AGC CAG GGT CTG GTC CAT TTT GGA CAG GGT CAG GAT CGG G | (SEQ ID NO: 35) |

The ligation was transformed into E. coli cells as described previously.

The DNA from the resulting transformants was isolated and the sequence was verified by DNA sequence analysis. The plasmid with the correct sequence was digested with NdeI and BamHI and the approximately 450 base-pair insert was recloned into an expression vector.

The protein was expressed in E.coli, isolated and was folded either by dilution into PBS or by dilution into 8M urea (both containing 5 mM cysteine) and exhaustive dialysis against PBS. Following final purification of the proteins by size exclusion chromatography the proteins were concentrated to 3–3.5 mg/mL in PBS. Amino acid composition was confirmed.

Preparation 5

The protein of SEQ ID NO: 6 with a Met Arg leader sequence was expressed in E.coli, isolated and folded as described previously. The Met Arg leader sequence was cleaved by the addition of 6–10 milliunits dDAP per mg of protein. The conversion reaction was allowed to proceed for 2–8 hours at room temperature. The progress of the reaction was monitored by high performance reversed phase chromatography. The reaction was terminated by adjusting the pH to 8 with NaOH. The des(Met-Arg) protein was further purified by cation exchange chromatography in 7–8M urea and size exclusion chromatography in PBS. Following final purification of the proteins by size exclusion chromatography the proteins were concentrated to 3–3.5 mg/mL in PBS.

Preferably, the DNA sequences are expressed with a dipeptide leader sequence encoding Met-Arg or Met-Tyr as described in U.S. Pat. No. 5,126,249, herein incorporated by reference. This approach facilitates the efficient expression of proteins and enables rapid conversion to the active protein form with Cathepsin C or other dipeptidylpeptidases. The purification of proteins is by techniques known in the art and includes reverse phase chromatography, affinity chromatography, and size exclusion.

The following examples are provided merely to further illustrate the preparation of the formuations of the invention.

The scope of the invention is not construed as merely consisting of the following examples.

EXAMPLE 1

Preparation of Zinc Formulations

A protein of SEQ ID NO: 6 (20 mg) (hereinafter Protein NO: 6) was completely dissolved in 32 mL of an aqueous solution containing 16 mg/mL glycerin and 2 mg/mL phenol and passed through a sterile 0.2μ filter. An aqueous solution containing 100 mg/mL of zinc in water was prepared from zinc chloride. Dilutions were made to prepare 10 mg/mL zinc and 1 mg/mL zinc solutions. Five 6-mL aliquots of the Protein No: 6 solution were modified as shown in Table I:

TABLE I

| Sample | μL of 1 mg/mL zinc added | μL of 10 mg/mL zinc added | μL of 100 mg/mL zinc added | μl of H$_2$O added | Total mg/mL zinc concentration |
|---|---|---|---|---|---|
| A | 0 | 0 | 0 | 100 | 0 |
| B | 17 | 0 | 0 | 83 | 0.0027 |
| C | 0 | 33 | 0 | 67 | 0.054 |
| D | 0 | 0 | 19 | 81 | 0.30 |
| E | 0 | 0 | 92 | 8 | 1.50 |

Each formulation was adjusted to pH 7.48±0.03 using small volumes of 2N and 5N sodium hydroxide and stored at 4° C. Sample A was completely clear while samples B through E were cloudy suspensions.

EXAMPLE 2

Analysis of Zinc Formulations

Size-exclusion chromatography was performed on the centrifuged supernatants of Samples A through E of Example 1. For these analyses, 100 μL of the supernatants were injected onto an analytical Superdex-75 (Pharmacia) column equilibrated in PBS (Dulbecco's Phosphate-Buffered Saline, GibcoBRL). The column was eluted at ambient temperature at 0.5 mL/min and the protein in the eluant monitored at 214 nm. The results of this analysis are shown in Table II.

TABLE II

| Sample | Percent of Protein NO: 6 Soluble in Supernatant |
|---|---|
| A | 100 |
| B | 36.7 |
| C | 0 |
| D | 0 |
| E | 0 |

EXAMPLE 3

Biological Activity of the Zinc Formulations

Doses (50 μL) of all five Samples in Example 1, each containing 30 μg of Protein No: 6, were injected subcutaneously into ob/ob mice in a single injection per day for four days. In addition, a 50-μL dose of a 16 mg/mL glycerin-2 mg/mL phenol solution adjusted to pH 7.4 was administered subcutaneously as a control. The average daily food intake and cumulative change in body weight from time zero for the ob/ob mice are shown in Table III.

TABLE III

| | Food Intake, g/mouse | | | | Weight Change, g/mouse | | | |
|---|---|---|---|---|---|---|---|---|
| Sample | Day 1 | Day 2 | Day 3 | Day 4 | Day 1 | Day 2 | Day 3 | Day 4 |
| Control | 4.9 | 4.7 | 5.2 | 5.2 | 0.2 | 0.3 | 1.2 | 1.0 |
| A | 4.5 | 3.8 | 3.1 | 2.9 | −0.2 | −0.5 | −0.6 | −1.7 |
| B | 3.7 | 3.3 | 3.3 | 3.1 | −0.6 | −0.8 | −1.2 | −1.7 |
| C | 4.0 | 3.2 | 2.8 | 2.3 | −0.6 | −0.7 | −1.2 | −2.3 |
| D | 3.3 | 2.4 | 1.4 | 1.0 | −1.0 | −1.7 | −2.9 | −4.3 |
| E | 4.3 | 2.6 | 1.3 | 0.7 | −1.0 | −1.7 | −3.3 | −4.8 |

The data demonstrate that the compounds of the present invention are potent and effective agents useful for treating obesity. When administered as a metal cation complex the potency of the protein was significantly enhanced. Increasing the total zinc concentration of the formulation also provides enhanced potency and improved biological effects in ob/ob mice. Accordingly, the present invention provides compounds, which comprise an obesity protein analog complexed with a divalent metal cation, pharmaceutical formulations thereof, and methods of using such compounds for treating obesity, and disorders associated with obesity such as diabetes (particularly non-insulin dependent diabetes mellitus), cardiovascular disease and cancer.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A compound comprising an obesity protein analog of formula I (SEQ. ID NO. 1) completed with a divalent metal cation.

2. A compound of claim 1, wherein the divalent metal cation is Zn++.

3. A compound of claim 2, wherein the analog is selected from the group consisting of SEQ ID NO:2, SEQ ID NO:3, SEQ ID NO:6, SEQ ID NO:7, SEQ ID NO:8, SEQ ID NO:9, SEQ ID NO:10, SEQ ID NO:11, SEQ ID NO:12, AND SEQ ID NO:13.

4. A compound of claim 3, wherein the analog is SEQ ID NO:6.

5. A formulation, comprising a compound of claim 1 and water.

6. A formulation, comprising a compound of claim 2 and water.

7. A formulation, comprising a compound of claim 3 and water.

8. A formulation, comprising a compound of claim 4 and water.

9. A formulation of claim 8, which further comprises a pharmaceutically acceptable preservative.

10. A formulation of claim 9 which further comprises an isotonicity agent.

11. A formulation of claim 10, which further comprises a physiologically acceptable buffer.

12. A formulation of claim 11, wherein the obesity protein analog is at a concentration of about 0.1 to 100 mg/mL and the preservative is phenol or m-cresol or a mixture thereof.

13. A formulation of claim 12, wherein the total cation concentration is 0.001 to 5.0 mg/mL.

14. A formulation of claim 13, wherein the total cation concentration is 0.05 to 1.5 mg/mL.

15. A formulation of claim 14, wherein the pH of the formulation is about pH 4.5 to 9.0.

16. A formulation of claim 15, wherein the pH of the formulation is about pH 5.5 to 8.0.

17. A formulation of claim 16, wherein the pH of the formulation is about pH 6.5 to 7.6.

18. A process of preparing a compound of claim 1, which comprises combining an obesity protein analog of formula I SEQ. ID NO: 1) and a divalent metal cation in an aqueous solution at a pH of about 4.5 to 9.0.

* * * * *

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 28
        ( D ) OTHER INFORMATION: /note= "Xaa at position 28 is Gln
            or absent;"

( x i ) SEQUENCE DESCRIPTION: SEQ ID NO:1:

```
Val  Pro  Ile  Gln  Lys  Val  Gln  Asp  Asp  Thr  Lys  Thr  Leu  Ile  Lys  Thr
 1              5                        10                       15

Ile  Val  Thr  Arg  Ile  Asn  Asp  Ile  Ser  His  Thr  Xaa  Ser  Val  Ser  Ser
               20                        25                       30

Lys  Gln  Lys  Val  Thr  Gly  Leu  Asp  Phe  Ile  Pro  Gly  Leu  His  Pro  Ile
              35                        40                       45

Leu  Thr  Leu  Ser  Lys  Met  Asp  Gln  Thr  Leu  Ala  Val  Tyr  Gln  Gln  Ile
     50                       55                       60
```

| Leu<br>65 | Thr | Ser | Met | Pro | Ser<br>70 | Arg | Asn | Val | Ile | Gln<br>75 | Ile | Ser | Asn | Asp | Leu<br>80 |

| Glu | Asn | Leu | Arg | Asp<br>85 | Leu | Leu | His | Val | Ala<br>90 | Phe | Ser | Lys | Ser<br>95 | Cys |

| His | Leu | Pro | Trp<br>100 | Ala | Ser | Gly | Leu | Glu<br>105 | Thr | Leu | Asp | Ser | Leu<br>110 | Gly | Gly |

| Val | Leu | Glu<br>115 | Ala | Ser | Gly | Tyr | Ser<br>120 | Thr | Glu | Val | Val | Ala<br>125 | Leu | Ser | Arg |

| Leu | Gln | Gly<br>130 | Ser | Leu | Gln | Asp<br>135 | Met | Leu | Trp | Gln | Leu<br>140 | Asp | Leu | Ser | Pro |

Gly Cys
145

(2) INFORMATION FOR SEQ ID NO:2:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

| Val<br>1 | Pro | Ile | Gln | Lys<br>5 | Val | Gln | Asp | Asp | Thr<br>10 | Lys | Thr | Leu | Ile | Lys<br>15 | Thr |

| Ile | Val | Thr | Arg<br>20 | Ile | Asp | Asp | Ile | Ser<br>25 | His | Thr | Gln | Ser | Val<br>30 | Ser | Ser |

| Lys | Gln | Lys<br>35 | Val | Thr | Gly | Leu | Asp<br>40 | Phe | Ile | Pro | Gly | Leu<br>45 | His | Pro | Ile |

| Leu | Thr<br>50 | Leu | Ser | Lys | Met | Asp<br>55 | Gln | Thr | Leu | Ala | Val<br>60 | Tyr | Gln | Gln | Ile |

| Leu<br>65 | Thr | Ser | Met | Pro | Ser<br>70 | Arg | Asn | Val | Ile | Gln<br>75 | Ile | Ser | Asn | Asp | Leu<br>80 |

| Glu | Asn | Leu | Arg | Asp<br>85 | Leu | Leu | His | Val | Leu<br>90 | Ala | Phe | Ser | Lys | Ser<br>95 | Cys |

| His | Leu | Pro | Trp<br>100 | Ala | Ser | Gly | Leu | Glu<br>105 | Thr | Leu | Asp | Ser | Leu<br>110 | Gly | Gly |

| Val | Leu | Glu<br>115 | Ala | Ser | Gly | Tyr | Ser<br>120 | Thr | Glu | Val | Val | Ala<br>125 | Leu | Ser | Arg |

| Leu | Gln | Gly<br>130 | Ser | Leu | Gln | Asp<br>135 | Met | Leu | Trp | Gln | Leu<br>140 | Asp | Leu | Ser | Pro |

Gly Cys
145

(2) INFORMATION FOR SEQ ID NO:3:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

| Val<br>1 | Pro | Ile | Gln | Lys<br>5 | Val | Gln | Asp | Asp | Thr<br>10 | Lys | Thr | Leu | Ile | Lys<br>15 | Thr |

| Ile | Val | Thr | Arg<br>20 | Ile | Asn | Asp | Ile | Ser<br>25 | His | Ala | Gln | Ser | Val<br>30 | Ser | Ser |

-continued

```
Lys  Gln  Lys  Val  Thr  Gly  Leu  Asp  Phe  Ile  Pro  Gly  Leu  His  Pro  Ile
          35                       40                      45

Leu  Thr  Leu  Ser  Lys  Met  Asp  Gln  Thr  Leu  Ala  Val  Tyr  Gln  Gln  Ile
     50                       55                      60

Leu  Thr  Ser  Met  Pro  Ser  Arg  Asn  Val  Ile  Gln  Ile  Ser  Asn  Asp  Leu
65                       70                      75                           80

Glu  Asn  Leu  Arg  Asp  Leu  Leu  His  Val  Leu  Ala  Phe  Ser  Lys  Ser  Cys
               85                            90                      95

His  Leu  Pro  Trp  Ala  Ser  Gly  Leu  Glu  Thr  Leu  Asp  Ser  Leu  Gly  Gly
               100                      105                     110

Val  Leu  Glu  Ala  Ser  Gly  Tyr  Ser  Thr  Glu  Val  Val  Ala  Leu  Ser  Arg
          115                      120                     125

Leu  Gln  Gly  Ser  Leu  Gln  Asp  Met  Leu  Trp  Gln  Leu  Asp  Leu  Ser  Pro
     130                      135                     140

Gly  Cys
145
```

( 2 ) INFORMATION FOR SEQ ID NO:4:

( i ) SEQUENCE CHARACTERISTICS:
( A ) LENGTH: 146 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Modified-site
( B ) LOCATION: 28
( D ) OTHER INFORMATION: /note= "Xaa at position 28 is Gln or absent;"

( x i ) SEQUENCE DESCRIPTION: SEQ ID NO:4:

```
Val  Pro  Ile  Gln  Lys  Val  Gln  Asp  Asp  Thr  Lys  Thr  Leu  Ile  Lys  Thr
1                   5                        10                      15

Ile  Val  Thr  Arg  Ile  Asn  Asp  Ile  Ser  His  Thr  Xaa  Ser  Val  Ser  Ser
               20                      25                      30

Lys  Gln  Lys  Val  Thr  Gly  Leu  Asp  Phe  Ile  Pro  Gly  Leu  His  Pro  Ile
          35                       40                      45

Leu  Thr  Leu  Ser  Lys  Met  Asp  Gln  Thr  Leu  Ala  Val  Tyr  Gln  Gln  Ile
     50                       55                      60

Leu  Thr  Ser  Met  Pro  Ser  Arg  Asn  Val  Ile  Gln  Ile  Ser  Asn  Asp  Leu
65                       70                      75                           80

Glu  Asn  Leu  Arg  Asp  Leu  Leu  His  Val  Leu  Ala  Phe  Ser  Lys  Ser  Cys
               85                            90                      95

His  Leu  Pro  Trp  Ala  Ser  Gly  Leu  Glu  Thr  Leu  Asp  Ser  Leu  Gly  Gly
               100                      105                     110

Val  Leu  Glu  Ala  Ser  Gly  Tyr  Ser  Thr  Glu  Val  Val  Ala  Leu  Ser  Arg
          115                      120                     125

Leu  Gln  Gly  Ser  Leu  Gln  Asp  Met  Leu  Trp  Gln  Leu  Asp  Leu  Ser  Pro
     130                      135                     140

Gly  Cys
145
```

( 2 ) INFORMATION FOR SEQ ID NO:5:

( i ) SEQUENCE CHARACTERISTICS:
( A ) LENGTH: 146 amino acids
( B ) TYPE: amino acid (C) STRANDEDNESS: single
(D) TOPOLOGY: linear (ii) MOLECULE TYPE: protein (xi) SEQUENCE DESCRIPTION: SEQ ID NO:5:

| Val | Pro | Ile | Gln | Lys | Val | Gln | Asp | Asp | Thr | Lys | Thr | Leu | Ile | Lys | Thr |
|---|---|---|---|---|---|---|---|---|---|---|---|---|---|---|---|
| 1 | | | | 5 | | | | | 10 | | | | | 15 | |
| Ile | Val | Thr | Arg | Ile | Asn | Asp | Ile | Ser | His | Thr | Gln | Ser | Val | Ser | Ser |
| | | | 20 | | | | | 25 | | | | | 30 | | |
| Lys | Gln | Lys | Val | Thr | Gly | Leu | Asp | Phe | Ile | Pro | Gly | Leu | His | Pro | Ile |
| | | 35 | | | | | 40 | | | | | 45 | | | |
| Leu | Thr | Leu | Ser | Lys | Met | Asp | Gln | Thr | Leu | Ala | Val | Tyr | Gln | Gln | Ile |
| | 50 | | | | | 55 | | | | | 60 | | | | |
| Leu | Thr | Ser | Met | Pro | Ser | Arg | Asn | Val | Ile | Gln | Ile | Ser | Asn | Asp | Leu |
| 65 | | | | | 70 | | | | | 75 | | | | | 80 |
| Glu | Asn | Leu | Arg | Asp | Leu | Leu | His | Val | Leu | Ala | Phe | Ser | Lys | Ser | Cys |
| | | | | 85 | | | | | 90 | | | | | 95 | |
| His | Leu | Pro | Trp | Ala | Ser | Gly | Leu | Glu | Thr | Leu | Asp | Ser | Leu | Gly | Gly |
| | | | 100 | | | | | 105 | | | | | 110 | | |
| Val | Leu | Glu | Ala | Ser | Gly | Tyr | Ser | Thr | Glu | Val | Val | Ala | Leu | Ser | Arg |
| | | 115 | | | | | 120 | | | | | 125 | | | |
| Leu | Gln | Gly | Ser | Leu | Gln | Asp | Met | Leu | Trp | Gln | Leu | Asp | Leu | Ser | Pro |
| | 130 | | | | | 135 | | | | | 140 | | | | |
| Gly | Cys | | | | | | | | | | | | | | |
| 145 | | | | | | | | | | | | | | | |

(2) INFORMATION FOR SEQ ID NO:6:

(i) SEQUENCE CHARACTERISTICS:
(A) LENGTH: 146 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:6:

| Val | Pro | Ile | Gln | Lys | Val | Gln | Asp | Asp | Thr | Lys | Thr | Leu | Ile | Lys | Thr |
|---|---|---|---|---|---|---|---|---|---|---|---|---|---|---|---|
| 1 | | | | 5 | | | | | 10 | | | | | 15 | |
| Ile | Val | Thr | Arg | Ile | Asn | Asp | Ile | Ser | His | Thr | Gln | Ser | Val | Ser | Ser |
| | | | 20 | | | | | 25 | | | | | 30 | | |
| Lys | Gln | Lys | Val | Thr | Gly | Leu | Asp | Phe | Ile | Pro | Gly | Leu | His | Pro | Ile |
| | | 35 | | | | | 40 | | | | | 45 | | | |
| Leu | Thr | Leu | Ser | Lys | Met | Asp | Gln | Thr | Leu | Ala | Val | Tyr | Gln | Gln | Ile |
| | 50 | | | | | 55 | | | | | 60 | | | | |
| Leu | Thr | Ser | Met | Pro | Ser | Arg | Asn | Val | Ile | Gln | Ile | Ser | Asn | Asp | Leu |
| 65 | | | | | 70 | | | | | 75 | | | | | 80 |
| Glu | Asn | Leu | Arg | Asp | Leu | Leu | His | Val | Leu | Ala | Phe | Ser | Lys | Ser | Cys |
| | | | | 85 | | | | | 90 | | | | | 95 | |
| His | Leu | Pro | Ala | Ala | Ser | Gly | Leu | Glu | Thr | Leu | Asp | Ser | Leu | Gly | Gly |
| | | | 100 | | | | | 105 | | | | | 110 | | |
| Val | Leu | Glu | Ala | Ser | Gly | Tyr | Ser | Thr | Glu | Val | Val | Ala | Leu | Ser | Arg |
| | | 115 | | | | | 120 | | | | | 125 | | | |
| Leu | Gln | Gly | Ser | Leu | Gln | Asp | Met | Leu | Trp | Gln | Leu | Asp | Leu | Ser | Pro |
| | 130 | | | | | 135 | | | | | 140 | | | | |
| Gly | Cys | | | | | | | | | | | | | | |
| 145 | | | | | | | | | | | | | | | |

( 2 ) INFORMATION FOR SEQ ID NO:7:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Val  Pro  Ile  Gln  Lys  Val  Gln  Asp  Asp  Thr  Lys  Thr  Leu  Ile  Lys  Thr
1              5                        10                       15
Ile  Val  Thr  Arg  Ile  Asn  Asp  Ile  Ser  His  Thr  Gln  Ser  Val  Ser  Ser
               20                       25                  30
Lys  Gln  Lys  Val  Thr  Gly  Leu  Asp  Phe  Ile  Pro  Gly  Leu  His  Pro  Ile
          35                       40                  45
Leu  Thr  Leu  Ser  Lys  Met  Asp  Gln  Thr  Leu  Ala  Val  Tyr  Gln  Gln  Ile
     50                       55                  60
Leu  Thr  Ser  Met  Pro  Ser  Arg  Asn  Val  Ile  Gln  Ile  Ser  Asn  Asp  Leu
65                  70                       75                            80
Glu  Asn  Leu  Arg  Asp  Leu  Leu  His  Val  Leu  Ala  Phe  Ser  Lys  Ser  Cys
               85                       90                            95
His  Leu  Pro  Gln  Ala  Ser  Gly  Leu  Glu  Thr  Leu  Asp  Ser  Leu  Gly  Gly
               100                      105                      110
Val  Leu  Glu  Ala  Ser  Gly  Tyr  Ser  Thr  Glu  Val  Val  Ala  Leu  Ser  Arg
          115                      120                 125
Leu  Gln  Gly  Ser  Leu  Gln  Asp  Met  Leu  Trp  Gln  Leu  Asp  Leu  Ser  Pro
     130                      135                      140
Gly  Cys
145
```

( 2 ) INFORMATION FOR SEQ ID NO:8:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Val  Pro  Ile  Gln  Lys  Val  Gln  Asp  Asp  Thr  Lys  Thr  Leu  Ile  Lys  Thr
1              5                        10                       15
Ile  Val  Thr  Arg  Ile  Asn  Asp  Ile  Ser  His  Thr  Gln  Ser  Val  Ser  Ser
               20                       25                  30
Lys  Gln  Lys  Val  Thr  Gly  Leu  Asp  Phe  Ile  Pro  Gly  Leu  His  Pro  Ile
          35                       40                  45
Leu  Thr  Leu  Ser  Lys  Met  Asp  Gln  Thr  Leu  Ala  Val  Tyr  Gln  Gln  Ile
     50                       55                  60
Leu  Thr  Ser  Met  Pro  Ser  Arg  Asn  Val  Ile  Gln  Ile  Ser  Asn  Asp  Leu
65                  70                       75                            80
Glu  Asn  Leu  Arg  Asp  Leu  Leu  His  Val  Leu  Ala  Phe  Ser  Lys  Ser  Cys
               85                       90                            95
His  Leu  Pro  Trp  Ala  Ser  Gly  Leu  Glu  Thr  Leu  Asp  Ser  Leu  Gly  Gly
               100                      105                      110
Val  Leu  Glu  Ala  Ser  Gly  Tyr  Ser  Thr  Glu  Val  Val  Ala  Leu  Ser  Arg
          115                      120                 125
```

37

-continued

```
Leu  Gln  Gly  Ser  Leu  Gln  Asp  Met  Leu  Gln  Gln  Leu  Asp  Leu  Ser  Pro
          130                      135                     140

Gly  Cys
145
```

(2) INFORMATION FOR SEQ ID NO:9:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Val  Pro  Ile  Gln  Lys  Val  Gln  Asp  Asp  Thr  Lys  Thr  Leu  Ile  Lys  Thr
1               5                        10                      15

Ile  Val  Thr  Arg  Ile  Asn  Asp  Ile  Ser  His  Thr  Gln  Ser  Val  Ser  Ser
          20                      25                      30

Lys  Gln  Lys  Val  Thr  Gly  Leu  Asp  Phe  Ile  Pro  Gly  Leu  His  Pro  Ile
          35                      40                      45

Leu  Thr  Leu  Ser  Lys  Met  Asp  Gln  Thr  Leu  Ala  Val  Tyr  Gln  Gln  Ile
          50                      55                      60

Leu  Thr  Ser  Met  Pro  Ser  Arg  Asn  Val  Ile  Gln  Ile  Ser  Asn  Asp  Leu
65                       70                      75                       80

Glu  Asn  Leu  Arg  Asp  Leu  Leu  His  Val  Leu  Ala  Phe  Ser  Lys  Ser  Cys
                    85                      90                      95

His  Leu  Pro  Gln  Ala  Ser  Gly  Leu  Glu  Thr  Leu  Asp  Ser  Leu  Gly  Gly
               100                     105                     110

Val  Leu  Glu  Ala  Ser  Gly  Tyr  Ser  Thr  Glu  Val  Val  Ala  Leu  Ser  Arg
          115                     120                     125

Leu  Gln  Gly  Ser  Leu  Gln  Asp  Met  Leu  Gln  Gln  Leu  Asp  Leu  Ser  Pro
          130                     135                     140

Gly  Cys
145
```

(2) INFORMATION FOR SEQ ID NO:10:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Val  Pro  Ile  Gln  Lys  Val  Gln  Asp  Asp  Thr  Lys  Thr  Leu  Ile  Lys  Thr
1               5                        10                      15

Ile  Val  Thr  Arg  Ile  Asn  Asp  Ile  Ser  His  Ala  Gln  Ser  Val  Ser  Ser
          20                      25                      30

Lys  Gln  Lys  Val  Thr  Gly  Leu  Asp  Phe  Ile  Pro  Gly  Leu  His  Pro  Ile
          35                      40                      45

Leu  Thr  Leu  Ser  Lys  Met  Asp  Gln  Thr  Leu  Ala  Val  Tyr  Gln  Gln  Ile
          50                      55                      60

Leu  Thr  Ser  Met  Pro  Ser  Arg  Asn  Val  Ile  Gln  Ile  Ser  Asn  Asp  Leu
65                       70                      75                       80

Glu  Asn  Leu  Arg  Asp  Leu  Leu  His  Val  Leu  Ala  Phe  Ser  Lys  Ser  Cys
                    85                      90                      95
```

```
His Leu Pro Ala Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Trp Gln Leu Asp Leu Ser Pro
    130                 135                 140

Gly Cys
145
```

(2) INFORMATION FOR SEQ ID NO:11:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
            85                  90                  95

His Leu Pro Ala Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Gln Gln Leu Asp Leu Ser Pro
    130                 135                 140

Gly Cys
145
```

(2) INFORMATION FOR SEQ ID NO:12:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
    50                  55                  60
```

| Leu | Thr | Ser | Met | Pro | Ser | Arg | Asn | Val | Ile | Gln | Ile | Ser | Asn | Asp | Leu |
|---|---|---|---|---|---|---|---|---|---|---|---|---|---|---|---|
| 65 | | | | | 70 | | | | | 75 | | | | | 80 |

| Glu | Asn | Leu | Arg | Asp | Leu | Leu | His | Val | Leu | Ala | Phe | Ser | Lys | Ser | Cys |
|---|---|---|---|---|---|---|---|---|---|---|---|---|---|---|---|
| | | | | 85 | | | | | 90 | | | | | 95 | |

| Ser | Leu | Pro | Gln | Thr | Ser | Gly | Leu | Glu | Thr | Leu | Asp | Ser | Leu | Gly | Gly |
|---|---|---|---|---|---|---|---|---|---|---|---|---|---|---|---|
| | | | 100 | | | | | 105 | | | | | 110 | | |

| Val | Leu | Glu | Ala | Ser | Gly | Tyr | Ser | Thr | Glu | Val | Val | Ala | Leu | Ser | Arg |
|---|---|---|---|---|---|---|---|---|---|---|---|---|---|---|---|
| | | 115 | | | | | 120 | | | | | 125 | | | |

| Leu | Gln | Gly | Ser | Leu | Gln | Asp | Met | Leu | Gln | Gln | Leu | Asp | Leu | Ser | Pro |
|---|---|---|---|---|---|---|---|---|---|---|---|---|---|---|---|
| | 130 | | | | | 135 | | | | | 140 | | | | |

| Gly | Cys |
|---|---|
| 145 | |

( 2 ) INFORMATION FOR SEQ ID NO:13:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

| Val | Pro | Ile | Gln | Lys | Val | Gln | Asp | Asp | Thr | Lys | Thr | Leu | Ile | Lys | Thr |
|---|---|---|---|---|---|---|---|---|---|---|---|---|---|---|---|
| 1 | | | | 5 | | | | | 10 | | | | | 15 | |

| Ile | Val | Thr | Arg | Ile | Asn | Asp | Ile | Ser | His | Thr | Gln | Ser | Val | Ser | Ser |
|---|---|---|---|---|---|---|---|---|---|---|---|---|---|---|---|
| | | | 20 | | | | | 25 | | | | | 30 | | |

| Lys | Gln | Lys | Val | Thr | Gly | Leu | Asp | Phe | Ile | Pro | Gly | Leu | His | Pro | Ile |
|---|---|---|---|---|---|---|---|---|---|---|---|---|---|---|---|
| | | 35 | | | | | 40 | | | | | 45 | | | |

| Leu | Thr | Leu | Ser | Lys | Met | Asp | Gln | Thr | Leu | Ala | Val | Tyr | Gln | Gln | Ile |
|---|---|---|---|---|---|---|---|---|---|---|---|---|---|---|---|
| | 50 | | | | | 55 | | | | | 60 | | | | |

| Leu | Thr | Ser | Met | Pro | Ser | Arg | Asn | Val | Ile | Gln | Ile | Ser | Asn | Asp | Leu |
|---|---|---|---|---|---|---|---|---|---|---|---|---|---|---|---|
| 65 | | | | | 70 | | | | | 75 | | | | | 80 |

| Glu | Asn | Leu | Arg | Asp | Leu | Leu | His | Val | Leu | Ala | Phe | Ser | Lys | Ser | Cys |
|---|---|---|---|---|---|---|---|---|---|---|---|---|---|---|---|
| | | | | 85 | | | | | 90 | | | | | 95 | |

| Ser | Leu | Pro | Gln | Ala | Ser | Gly | Leu | Glu | Thr | Leu | Asp | Ser | Leu | Gly | Gly |
|---|---|---|---|---|---|---|---|---|---|---|---|---|---|---|---|
| | | | 100 | | | | | 105 | | | | | 110 | | |

| Val | Leu | Glu | Ala | Ser | Gly | Tyr | Ser | Thr | Glu | Val | Val | Ala | Leu | Ser | Arg |
|---|---|---|---|---|---|---|---|---|---|---|---|---|---|---|---|
| | | 115 | | | | | 120 | | | | | 125 | | | |

| Leu | Gln | Gly | Ser | Leu | Gln | Asp | Met | Leu | Gln | Gln | Leu | Asp | Leu | Ser | Pro |
|---|---|---|---|---|---|---|---|---|---|---|---|---|---|---|---|
| | 130 | | | | | 135 | | | | | 140 | | | | |

| Gly | Cys |
|---|---|
| 145 | |

( 2 ) INFORMATION FOR SEQ ID NO:14:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

```
GTGCTGGCCT TCTCTAAAAG TTGCCACTTG CCAGCTGCCA GTGGCCTGGA GACATTGGAC      60
AGTCTGGGGG GAGTCCTGGA AGCC                                              84
```

( 2 ) INFORMATION FOR SEQ ID NO:15:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:15:

```
TGAGGCTTCC AGGACTCCCC CCAGACTGTC CAATGTCTCC AGGCCACTGG CAGCTGGCAA      60
GTGGCAACTT TTAGAGAAGG CCAGCAC                                         87
```

( 2 ) INFORMATION FOR SEQ ID NO:16:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

```
TATGAGGGTA CCTATCCAAA AAGTACAAGA TGACACCAAA ACACTGATAA AGACAATAGT      60
CACAAG                                                                66
```

( 2 ) INFORMATION FOR SEQ ID NO:17:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

```
GATAGATGAT ATCTCACACA CACAGTCAGT CTCATCTAAA CAGAAAGTCA CAGGCTTGGA      60
CTTCATACCT GG                                                         72
```

( 2 ) INFORMATION FOR SEQ ID NO:18:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

```
GCTGCACCCC ATACTGACAT TGTCTAAAAT GGACCAGACA CTGGCAGTCT ATCAACAGAT      60
CTTAACAAGT ATGCCTT                                                    77
```

( 2 ) INFORMATION FOR SEQ ID NO:19:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

```
CTAGAAGGCA TACTTGTTAA GATCTGTTGA TAGACTGC                              38
```

( 2 ) INFORMATION FOR SEQ ID NO:20:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

```
CAGTGTCTGG TCCATTTTAG ACAATGTCAG TATGGGGTGC AGCCCAGGTA TGAAGTCCAA    60
GC                                                                  62
```

( 2 ) INFORMATION FOR SEQ ID NO:21:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

```
CTGTGACTTT CTGTTTAGAT GAGACTGACT GTGTGTGTGA GATATCATCT ATCCTTGTGA    60
CTATTGTCTT TATCAGTGTT TTG                                           83
```

( 2 ) INFORMATION FOR SEQ ID NO:22:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

```
GTGTCATCTT GTACTTTTTG GATAGGTACC CTCA                               34
```

( 2 ) INFORMATION FOR SEQ ID NO:23:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

```
CTAGAAACGT GATACAAATA TCTAACGACC TGGAGAACCT GCGGGATCTG CTGCACGTGC    60
TGGCCTTCTC TAAAAGTTGC CACTTGCCAT GG                                 92
```

( 2 ) INFORMATION FOR SEQ ID NO:24:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

GCCAGTGGCC TGGAGACATT GGACAGTCTG GGGGGAGTCC TGGAAGCCTC AGGCTATTCT 60

ACAGAGGTGG TGGC 74

( 2 ) INFORMATION FOR SEQ ID NO:25:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

CCTGAGCAGG CTGCAGGGGT CTCTGCAAGA CATGCTGTGG CAGCTGGACC TGAGCCCCGG 60

GTGCTAATAG 70

( 2 ) INFORMATION FOR SEQ ID NO:26:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

GATCCTATTA GCACCCGGGG CTCAGGTCCA GCTGCCACAG CATGTCTTGC AGAGACC 57

( 2 ) INFORMATION FOR SEQ ID NO:27:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

CCTGCAGCCT GCTCAGGGCC ACCACTCTG TAGAATAGCC TGAGGCTTCC AGGACTCCC 59

( 2 ) INFORMATION FOR SEQ ID NO:28:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

CCCAGACTGT CCAATGTCTC CAGGCCACTG GCCCATGGCA AGTGGCAACT TTTAGAGAAG 60

G 61

( 2 ) INFORMATION FOR SEQ ID NO:29:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

CCAGCACGTG CAGCAGATCC CGCAGGTTCT CCAGGTCGTT AGATATTTGT ATCACGTTT 59

(2) INFORMATION FOR SEQ ID NO:30:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

TATGCGGGTA CCGATCCAGA AAGTTCAGGA CGACACCAAA ACCCTGATCA AAACCATCGT 60

TAC 63

(2) INFORMATION FOR SEQ ID NO:31:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GCGTATCAAC GACATCTCCC ACACCCAGTC CGTGAGCTCC AAACAGAAGG TTACCGGTCT 60

GGACTTCATC CCGG 74

(2) INFORMATION FOR SEQ ID NO:32:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

GTCTGCACCC GATCCTGACC CTGTCCAAAA TGGACCAGAC CCTGGCTGTT TACCAGCA 58

(2) INFORMATION FOR SEQ ID NO:33:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

ATACGCGTAA CGATGGTTTT GATCAGGGTT TTGGTGTCGT CCTGAACTTT CTGGATCGGT 60

ACCCGCA 67

(2) INFORMATION FOR SEQ ID NO:34:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

TGCAGACCCG GGATGAAGTC CAGACCGGTA ACCTTCTGTT TGGAGCTCAC GGACTGGGTG 60

TGGGAGATGT CGTTG 75

(2) INFORMATION FOR SEQ ID NO:35:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

GATCTGCTGG TAAACAGCCA GGGTCTGGTC CATTTTGGAC AGGGTCAGGA TCGGG 55